US006352832B1

(12) United States Patent
LaRosa et al.

(10) Patent No.: US 6,352,832 B1
(45) Date of Patent: Mar. 5, 2002

(54) ANTI-CCR2 ANTIBODIES AND METHODS OF USE THEREFOR

(75) Inventors: Gregory J. LaRosa, West Roxbury; Christopher Horvath, Taunton; Walter Newman, Boston, all of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/359,193

(22) Filed: Jul. 22, 1999

Related U.S. Application Data

(63) Continuation-in-part of application No. 09/121,781, filed on Jul. 23, 1998.

(51) Int. Cl.$^7$ ................................................ G01N 33/53
(52) U.S. Cl. ...................... 435/7.1; 435/5; 435/345; 435/343; 435/343.2; 436/548
(58) Field of Search ........................... 435/5, 7.1, 345, 435/343, 343.2; 436/548

(56) References Cited

U.S. PATENT DOCUMENTS

| | | | | |
|---|---|---|---|---|
| 5,440,021 A | 8/1995 | Chuntharapai et al. | 530/388.22 |
| 5,543,503 A | 8/1996 | Chuntharapai et al. | 530/388.22 |
| 5,571,713 A | 11/1996 | Lyle et al. | ................ | 435/240.2 |
| 5,707,815 A | 1/1998 | Charo et al. | .................. | 435/7.2 |
| 6,084,075 A | 7/2000 | Lind et al. | ............. | 530/388.22 |

FOREIGN PATENT DOCUMENTS

| | | |
|---|---|---|
| WO | WO 94/09128 | 4/1994 |
| WO | WO 95/08576 | 3/1995 |
| WO | WO95/19436 | 7/1995 |
| WO | WO97/31949 | 9/1997 |
| WO | WO 98/44953 | 10/1998 |
| WO | WO 99/15666 | 4/1999 |

OTHER PUBLICATIONS

Welt, et al., "Targeting CCR–2 and CD18 Inhibits Experimental in–Stent Restenosis in Primates. Inhibitory Potential Depends on Type of Injury and Leukocytes Targeted", *Circulation–Journal of the American Heart Association* (Abstracts from Scientific Sessions 2000), 102(18): II–247, Abstract 1206 (2000).

Monteclaro, Felipe S. and Charo, Israel F., "The Amino–Terminal Domain of CCR2 Is Both Necessary and Sufficient for High Affinity Binding of Monocyte Chemoattractant Protein 1", *The Journal of Biological Chemistry*, 272(37):23186–23190 (1997).

Qin, Shixin, et al., "Expression of Monocyte Chemoattractant Protein–1 and Interleukin–8 Receptors on Subsets of T Cells: Correlation with Transendothelial Chemotactic Potential", *Eur. J. Immonol.*, 26:640–647 (1996).

Yamagami, Shinsuke, et al., "cDNA Cloning and Functional Expression of a Human Monocyte Chemoattractant Protein 1 Receptor", *Biochemical and Biophysical Research Communications*, 202(2):1156–1162 (1994).

Charo, Israel F., et al., "Molecular Cloning and Functional Expression of Two Monocyte Chemoattractant Protein 1 Receptors Reveals Alternative Splicing of the Carboxyl–Terminal Tails", *Proc. Natl. Acad. Sci., USA.*, 91:2752–2756 (1994).

Aragay, A.M., et al., "Monocyte Chemoattractants Protein–1–Induced CCR2B Receptor Desensitization Mediated by the G Protein–Coupled Receptor Kinase 2", *Proc. Natl. Acad. Sci., USA*, 95:2984–2990 (1998).

Frade, Jose M.R., et al., "Characterization of the CCR2 Chemokine Receptor: Functional CCR2 Receptor Expression in B Cells", *J. Immunol.*, 159(11):5576–5584 (1997).

Frade, José M.R., et al., "The Amino–Terminal Domain of the CCR2 Chemokine Receptor Acts as Coreceptor for HIV–1 Infection", *J. Clin. Invest.*, 100(3):497–502 (1997).

Wong, Lu–Min, et al., "Organization and Differential Expression of the Human Monocyte Chemoattractant Protein 1 Receptor Gene", *The Journal of Biological Chemistry*, 272(2):1038–1045 (1997).

Kurihara, Takao and Bravo, Rodrigo, "Cloning and Functional Expression of mCCR2, a Murine Receptor for the C–C Chemokines JE and FIC", *The Journal of Biological Chemistry*, 271(20):11603–11606 (1996).

Förster, R., et al., "A general method for screening mAbs specific for G–protein coupled receptors as exemplified by using epitope tagged BLR1–transfected 293 cells and solid–phase cell ELISA", *Biochemical and Biophysical Research Communications*, 196(3):1496–1503 (1993).

Boring, L., et al., "Decreased lesion formation in CCR2$^{-/-}$ mice reveals a role for chemokines in the initiation of atherosclerosis," *Nature*, 394(27):894–897 (1998).

Yla–Herttuala, S., et al., "Expression of monocyte chemoattractant protein 1 in macrophage–rich areas of human and rabbit atherosclerotic lesions," *Proc. Natl. Acad. Sci., USA*, 88:5252–5256 (1991).

Taubman, M.B., et al., "JE mRNA Accumulates Rapidly in Aortic Injury and in Platelet–Derived Growth Factor–Stimulated Vascular Smooth Muscle Cells," *Circulation Research* 70(2):314–325 (1992).

(List continued on next page.)

*Primary Examiner*—Ali R. Salimi
(74) *Attorney, Agent, or Firm*—Hamilton, Brook, Smith & Reynolds, P.C.

(57) ABSTRACT

The present invention relates to an antibody or functional fragment thereof which binds to a mammalian (e.g., human) CC-chemokine receptor 2 (CCR2) or a portion of the receptor and blocks binding of a ligand to the receptor. The invention further relates to a method of inhibiting the interaction of a cell bearing mammalian CCR2 with a ligand thereof, and to use of the antibodies and fragments in therapeutic, prophylactic and diagnostic methods.

72 Claims, 15 Drawing Sheets

OTHER PUBLICATIONS

Feng, A., et al., "Red Wine Inhibits Monocyte Chemotactic Protein–1 Expression and Modestly Reduces Neointimal Hyperplasia After Balloon Injury in Cholestreol–Fed Rabbits," *Circulation* 100:2254–2259 (1999).

Lukacs, N.W., et al., "Production of Monocyte Chemoattractant Protein–1 and Macrophage Inflammatory Protein–1α by Inflammatory Granuloma Fibroblasts," *American Journal of Pathology*, 144(4):711–718 (1994).

Koch, A.E., et al., "Enhanced Production of Monocyte Chemoattractant Protein–1 in Rheumatoid Arthritis," *The Jour. of Clin. Invest.*, 90:772–779 (1992).

Harigai, M., et al., "Monocyte Chemoattractant Protein–1 (MCP–1) in Inflammatory Joint Diseases and Its Involvement in the Cytokine Network of Rheumatoid Synovium," *Clin. Immun. and Immunopathology*, Rose,69(1):83–91 (1993).

Villiger, P.M., et al., "Production of Monocyte Chemoattractant Protein–1 by Inflamed Synovial Tissue and Cultured Synoviocytes," *The Jour. Of Immun.* 149(2):722–727 (1992).

Reinecker, H.C., et al., "Monocyte–Chemoattractant Protein–1 Gene Expression in Intestinal Epithelial Cells and Inflammatory Bowel Disease Mucosa," *Gastroenterology*, 108(1):40–50 (1995).

Nelken, N.A., et al., "Monocyte Chemoattractant Protein–1 in Human Atheromatous Plaques," *J. Clin. Invest.*, 88:1121–1127 (1991).

Grewal, I.S. et al., "Transgenic Monocyte Chemoattractant Protein–1 (MCP–1) in Pancreatic Islets Produces Monocyte–Rich Insulitis Without Diabetes," *J. Immunol.*, 159:401–408 (1997).

Yu, X., et al., "Elevated expression of monocyte chemoattractant protein 1 by vascular smooth muscle cells in hypercholesterolemic primates," *Proc. Natl. Acad. Sci., USA*, 89:6953–6957 (1992).

Berman, J.W., et al., "Localization of Monocyte Chemoattractant Peptide–1 Expression in the Central Nervous System in Experimental Autoimmune Encephalomyelitis and Trauma in the Rat," *J. Immunol.*, 156:3017–3023 (1996).

Lukacs, N.W., et al., "The Production of Chemotactic Cytokines an Allogeneic Response," *Amer. Jour. of Pathology*, 143(4):1179–1188 (1993).

Christensen, P.J., et al., "Characterization of the Production of Monocyte Chemoattractant Protein–1 and IL–8 in an Allogeneic Immune Response," *The Journal of Immunology*, 151(3):1205–1213 (1993).

Rand, M.L., et al., "Inhibition of T Cell Recruitment and Cutaneous Delayed–Type Hypersensitivity–Induced Inflammation with Antibodies to Monocyte Chemoattractant Protein–1," *Amer. Jour. of Pathology*, 148(3):855–864 (1996).

Jones, M.L., and Warren, J.S., "Monocyte Chemoattractant Protein 1 in a Rat Model of Pulmonary Granulomatosis," *Laboratory Investigation*, 66(4):498–503 (1992).

Lloyd, C.M., et al., "Role of MCP–1 and RANTES in inflammation and progression to fibrosis during murine crescentic nephritis," *Journal of Leukocyte Biology*, 62:676–680 (1997).

Flory, C.M., et al., "Pulmonary Granuloma Formation in the Rat is Partially Dependent on Monocyte Chemoattractant Protein 1," *Laboratory Invest.*, 69(4):396–404 (1993).

Jones, M.L., et al., "Potential Role of Monocyte Chemoattractant Protein 1/JE In Monocyte–Macrophage–Dependent IgA Immune Complex Alveolitis in the Rat," *The Jour. of Immun.*, 149(6):2147–2154 (1992).

Gu, L., et al., "Absence of Monocyte Chemoattractant Protein–1 Reduces Atherosclerosis in Low Density Lipoprotein Receptor–Deficient Mice," *Molecular Cell*, 2(2):275–281 (1998).

Tesch, G.H., et al., "Monocyte chemoattractant protein–1 promotes macrophage–mediated tubular injury, but not glomerular injury, in nephrotoxic serum nephritis," *The Jour. of Clin. Invest.*, 103(1):73–80 (1999).

Lu, B., et al., "Abnormalities in Monocyte Recruitment and Cytokine Expression in Monocyte Chemoattractant Protein 1–deficient Mice," *The Jour. Exp. Med.*, 187(4):601–608 (1998).

Rutledge, B.J., et al., "High Level Monocyte Chemoattractant Protein–1 Expression in Transgenic Mice Increases Their Susceptibility to Intracellular Pathogens," *The Jour. of Immun.*, 155:4838–4843 (1995).

Gunn, M.D., et al., "Monocyte Chemoattractant Protein–1 Is Sufficient for the Chemotaxis of Monocytes and Lymphocytes in Transgenic Mice but Requires an Additional Stimulus for Inflammatory Activation," *The Jour. of Immun.*, 158:376–383 (1997).

Chensue, S.W., et al., "Role of Monocyte Chemoattractant Protein–1 (MCP–1) in Th1 (Mycobacterial) and Th2 (Schistosomal) Antigen–Induced Granuloma Formation," *The Jour. of Immun.*, 157:4602–4608 (1996).

Lukacs, N.W., et al., "Differential Recruitment of Leukocyte Populations and Alteration of Airway Hyperreactivity by C–C Family Chemokines in Allergic Airway Inflammation," *The Jour. of Immun.*, 158:4398–4404 (1997).

Tang, W.W., et al., "Chemokine Expression in Experimental Tubulointerstitial Nephritis," *The Jour. of Immun.*, 159:870–876 (1997).

Fujinaka, H., et al., "Suppression of Anti–Glomerular Basement Membrane Nephritis by Administration of Anti–Monocyte Chemoattractant Protein–1 Antibody in WKY Rats," *Jour. of the Amer. Soc. of Nephrology*, 8:1174–1178 (1997).

Lloyd, C.M., et al., "RANTES and Monocyte Chemoattractant Protein–1 (MCP–1) Play an Important Role in the Inflammatory Phase of Crescentic Nephritis, but Only MCP–1 Is Involved in Crescent Formation and Interstitial Fibrosis," *The Jour. of Exp. Med.*, 185(7):1371–1380 (1997).

Furukawa, Y., et al., "Anti–Monocyte Chemoattractant Protein–1/Monocyte Chemotactic and Activating Factor Antibody Inhibits Neointimal Hyperplasia in Injured Rat Carotid Arteries," *Circulation Research*, 84:306–314 (1999).

Schimmer, R.C., et al., "Streptococcal Cell Wall–Induced Arthritis: Requirements for IL–4, IL–10, IFN–γ, and Monocyte Chemoattractant Protein–1," *The Jour. of Immunology*, 160:1466–1471 (1998).

Ogata, H., et al., "The Role of Monocyte Chemoattractant Protein–1 (MCP–1) in the Pathogenesis of Collagen–Induced Arthritis in Rats," *Jour. of the Pathology Soc.*, 182:106–114 (1997).

Huffnagle, G.B., et al., "The Role of Monocyte Chemotactic Protein–1 (MCP–1) in the Recruitment of Monocytes and CD4⁺ T Cells During a Pulmonary *Cryptococcus neoformans* Infection," *The Jour. of Immun.*, 155:4790–4797 (1995).

Gong, J., et al., "An Antagonist of Monocyte Chemoattractant Protein 1 (MCP–1) Inhibits Arthritis in the MRL–lpr Mouse Model," *The Jour. of Exper. Med.*, 186(1):131–137 (1997).

Boring, L., et al., "Impaired Monocyte Migration and Reduced Type 1 (Th1) Cytokine Response in C–C Chemokine Receptor 2 Knockout Mice," *The Jour. of Clin. Invest.*, 100(10):2552–2561 (1997).

Kuziel, W.A., et al., "Severe reduction in leukocyte adhesion and monocyte extravasation in mice deficient in CC chemokine receptor 2," *Proc. Natl. Acad. of Sci.*, USA 94(22):12053–12058 (1997).

Kurihara, T., et al., "Defects in Macrophage Recruitment and Host Defense in Mice Lacking the CCR2 Chemokine Receptor," *The Jour. of Experi. Med.*, 186(10):1757–1762 (1997).

Zisman, D.A., et al., "MCP–1 Protects Mice in Lethal Endotoxemia," *The Jour. of Clin. Invest.*, 99(12):2832–2836 (1997).

Jiang, Y., et al., "Chemokine receptor expression in cultured glia and rat experimental allergic encephalomyelitis," *Jour. of Neuroimmunology*, 86:1–12, (1998).

Chuntharapai, et al., "Generation of Monoclonal Antibodies to Chemokine Receptors", *Methods in Enzymology* 288: 15–27 (1997).

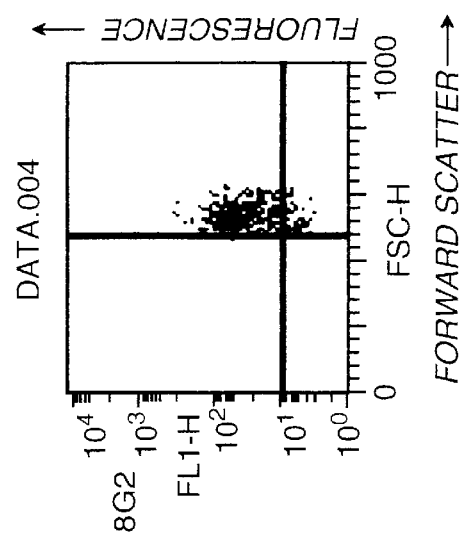
FIG. 2L MONOCYTES
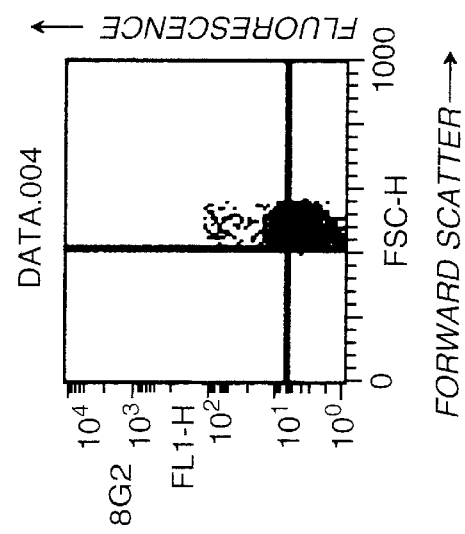
FIG. 2K GRANULOCYTES
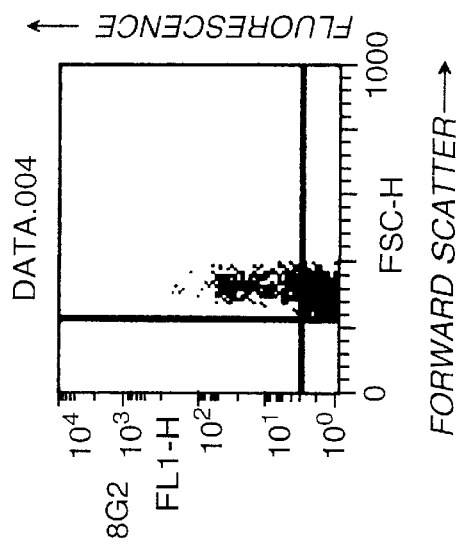
FIG. 2J LYMPHOCYTES

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1 gagacaagc cacaagctga ac     22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
tctgtattag tacacacagc cc     22

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
atgctgtcca catctcgttc tcgg     24

<210> SEQ ID NO 4
<211> LENGTH: 27
<212> TYPE: DNA
<213> ORGANISM: Artificial Sequence
<220> FEATURE:
<223> OTHER INFORMATION: Primer

```
<400> SEQUENCE: 4
ttataaacca gccgagactt cctgctc                                              27

<210> SEQ ID NO 5
<211> LENGTH: 24
<212> TYPE: PRT
<213> ORGANISM: Homo sapiens

<400> SEQUENCE: 5

Met Pro Met Gly Ser Leu Gln Pro Leu Ala Thr Leu Tyr Leu Leu Gly
 1               5                  10                  15

Met Leu Val Ala Ser Val Leu Ala
             20

<210> SEQ ID NO 6
<211> LENGTH: 60
<212> TYPE: DNA
<213> ORGANISM: Artificial Sequence
<220> FEATURE:
<223> OTHER INFORMATION: Primer

<400> SEQUENCE: 6
ggggatccag aaaccatgcc catggggtct ctgcaaccgc tggccacctt gtacctgctg          60

<210> SEQ ID NO 7
<211> LENGTH: 65
<212> TYPE: DNA
<213> ORGANISM: Artificial Sequence
<220> FEATURE:
<223> OTHER INFORMATION: Primer

<400> SEQUENCE: 7
gccaccttgt acctgctggg gatgctggtc gcttccgtgc tagcgatgct gtccacatct          60
cgttc                                                                     65

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
gacgaccagc atgttgcc                                                       18
```

ANTI-CCR2 ANTIBODIES AND METHODS OF USE THEREFOR

RELATED APPLICATIONS

This application is a continuation-in-part of U.S. patent application Ser. No. 09/121,781, filed Jul. 23, 1998, the entire teachings of which are incorporated herein by reference in their entirety.

BACKGROUND OF THE INVENTION

Over the past several years a growing family of leukocyte chemoattractant/activating factors, termed chemokines, has been described (Oppenheim, J. J. et al., *Annu. Rev. Immunol.,* 9:617–648 (1991); Schall and Bacon, *Curr. Opin. Immunol.,* 6:865–873 (1994); Baggiolini, M., et al., *Adv. Imunol.,* 55:97–179 (1994)). Members of this family are produced and secreted by many cell types in response to early inflammatory mediators such as IL-1β or TNFα. The chemokine superfamily comprises two main branches: the α-chemokines (or CXC chemokines) and the β-chemokines (CC chemokines). The α-chemokine branch includes proteins such as IL-8, neutrophil activating peptide-2 (NAP-2), melanoma growth stimulatory activity (MGSA/gro or GROα), and ENA-78, each of which have attracting and activating effects predominantly on neutrophils. The members of the β-chemokine branch affect other cell types such as monocytes, lymphocytes, basophils, and eosinophils (Oppenheim, J. J. et al., *Annu. Rev. Immunol.,* 9:617–648 (1991); Baggiolini, M., et al., *Adv. Imunol.,* 55:97–179 (1994); Miller and Krangel, *Crit. Rev. Immunol.,* 12:17–46 (1992); Jose, P. J., et al., *J. Exp. Med.,* 179:881–118 (1994); Ponath, P. D., et al., *J. Clin. Invest.,* 97:604–612 (1996)), and include proteins such as monocyte chemotactic proteins 1–4 (MCP-1, MCP-2, MCP-3, and MCP-4), RANTES, and macrophage inflammatory proteins (MIP-1α, MIP-1β). Recently a new class of membrane-bound chemokines designated CX3C chemokines has been identified (Bazan, J. F., et al., *Nature* 385:640–644 (1997)). Chemokines can mediate a range of pro-inflammatory effects on leukocytes, such as triggering of chemotaxis, degranulation, synthesis of lipid mediators, and integrin activation (Oppenheim, J. J. et al., *Annu. Rev. Immunol.,* 9:617–648 (1991); Baggiolini, M., et al., *Adv. Imunol.,* 55:97–179 (1994); Miller, M. D. and Krangel, M. S., *Crit. Rev. Immunol.,* 12:17–46 (1992)). Lately, certain β-chemokines have been shown to suppress HIV-1 infection of human T cell lines in vitro (Cocchi, F., et al., *Science* (Wash. D.C.), 270:1811–1815 (1995)).

Chemokines bind to 7 transmembrane spanning (7TMS) G protein-coupled receptors (Murphy, P. M., *Annu. Rev. Immunol.,* 12:593–633 (1994)). Some known receptors for the CC or β chemokines include CCR1, which binds MIP-1α and RANTES (Neote, K., et al., *Cell,* 72:415–425 (1993); Gao, J. L., *J. Exp. Med.,* 177:1421–1427 (1993)); CCR2, which binds chemokines including MCP-1, MCP-2, MCP-3 and MCP-4 (Charo, I. F., et al., *Proc. Natl. Acad. Sci. USA,* 91:2752–2756 (1994); Myers, S. J., et al., *J. Biol. Chem.,* 270:5786–5792 (1995); Gong et al., *J. Biol Chem* 272:11682–11685 (1997); Garcia-Zepeda et al., *J. Immunol.* 157:5613–5626 (1996)); CCR3, which binds chemokines including eotaxin, RANTES and MCP-3 (Ponath, P. D., et al., *J. Exp. Med.,* 183:2437–2448 (1996)); CCR4, which has been found to signal in response to MCP-1, MIP-1α, and RANTES (Power, C. A., et al., *J. Biol. Chem.,* 270:19495–19500 (1995)); and CCR5, which has been shown to signal in response to MIP-1α, MIP-1β and RANTES (Boring, L., et al., *J. Biol. Chem.,* 271 (13) :7551–7558 (1996); Raport, C. J., *J. Biol. Chem.,* 271:17161–17166 (1996); and Samson, M. et al., *Biochemistry,* 35:3362–3367 (1996)).

CCR2 is expressed on the surface of several leukocyte subsets, and appears to be expressed in two slightly different forms (CCR2a and CCR2b) due to alternative splicing of the mRNA encoding the carboxy-terminal region (Charo et al., *Proc. Natl. Acad. Sci. USA* 91:2752–2756 (1994)). MCP-1 acts upon monocytes, lymphocytes and basophils, inducing chemotaxis, granule release, respiratory burst and histamine and cytokine release. Studies have suggested that MCP-1 is implicated in the pathology of diseases such as rheumatoid arthritis, atherosclerosis, granulomatous diseases and multiple sclerosis (Koch, *J. Clin. Invest.* 90:772–79 (1992); Hosaka et al., *Clin. Exp. Immunol.* 97:451–457 (1994); Schwartz et al., *Am. J. Cardiol.* 71(6):9B–14B (1993); Schimmer et al., *J. Immunol.* 160:1466–1471 (1998); Flory et al., *Lab. Invest.* 69:396–404 (1993); Gong et al., *J. Exp. Med.* 186:131–137 (1997)). Additionally, CCR2 can act as a co-receptor for HIV (Connor et al., *J. Exp. Med.* 185:621–628 (1997)). Thus, CCR2 receptor antagonists may represent a new class of important therapeutic agents.

SUMMARY OF THE INVENTION

The present invention relates to an antibody (immunoglobulin) or functional fragment thereof (e.g., an antigen-binding fragment) which binds to a mammalian CC-chemokine receptor 2 (also referred to as CCR2, CKR-2, MCP-1RA or MCP-1RB) or portion of the receptor (anti-CCR2). In one embodiment, the antibody of the present invention or fragment thereof has specificity for human or rhesus CCR2 or a portion thereof. In another embodiment, the antibody or fragment of the invention blocks binding of a ligand (e.g., MCP-1, MCP-2, MCP-3, MCP-4) to the receptor and inhibits function associated with binding of the ligand to the receptor (e.g., leukocyte trafficking). For example, as described herein, antibodies and fragments thereof of the present invention which bind human or rhesus CCR2 or a portion thereof, can block binding of a chemokine (e.g., MCP-1, MCP-2, MCP-3, MCP-4) to the receptor and inhibit function associated with binding of the chemokine to the receptor. In one embodiment, the antibody is monoclonal antibody (mAb) LS132.1D9 (1D9) or an antibody which can compete with 1D9 for binding to human CCR2 or a portion of human CCR2. Functional fragments of the foregoing antibodies are also envisioned.

In another embodiment, the antibody or functional fragment of the present invention binds human CCR2 or a portion thereof, and inhibits human immunodeficiency virus (HIV) binding to the receptor, thereby inhibiting function associated with binding of HIV to the receptor (e.g., HIV antigen release and infectivity). In one embodiment, the antibody is monoclonal antibody 1D9 or an antibody which can compete with 1D9 for binding to human CCR2 or a portion of human CCR2.

The present invention also relates to an antibody or functional fragment thereof (e.g., an antigen-binding fragment) which binds to a mammalian CCR2 or portion of the receptor and provides increased fluorescent staining intensity of CCR2 or compositions comprising CCR2 relative to other anti-CCR2 antibodies. In one embodiment, the antibody is monoclonal antibody 1D9 or LS132.8G2 (8G2) or an antibody which can compete with 1D9 or 8G2 for binding to human CCR2 or a portion of human CCR2.

The present invention further relates to a method of inhibiting the interaction of a cell bearing mammalian (e.g., human, non-human primate or murine) CCR2 with a ligand thereof, comprising contacting the cell with an effective amount of an antibody or functional fragment thereof which binds to a mammalian CCR2 or a portion of CCR2. Suitable cells include granulocytes, leukocytes, such as monocytes, macrophages, basophils and eosinophils, mast cells, and lymphocytes including T cells (e.g., CD8+ cells, CD4+ cells, CD25+ cells, CD45RO+ cells), and other cells expressing CCR2 such as a recombinant cell expressing CCR2 (e.g., transfected cells). In a particular embodiment, the antibody is 1D9 or an antibody which can compete with 1D9 for binding to human CCR2 or a portion of human CCR2.

Another embodiment of the invention relates to a method of inhibiting the interaction of a cell bearing mammalian CCR2 with a chemokine, comprising contacting said cell with an effective amount of an antibody or functional fragment thereof which binds to CCR2 or a portion of said receptor. In one embodiment of the method, the antibody or functional fragment thereof is any one or more of 1D9, an antigen-binding fragment of 1D9 or an antibody or fragment thereof having an epitopic specificity which is the same as or similar to that of 1D9. Furthermore, the invention relates to a method of inhibiting a function associated with binding of a chemokine to CCR2, comprising administering an effective amount of an antibody or functional fragment thereof which binds to a mammalian CCR2 protein or a portion of said receptor. In one aspect of the method, the antibody or functional fragment thereof is any one or more of 1D9, an antigen-binding fragment of 1D9 or an antibody or fragment thereof having an epitopic specificity which is the same as or similar to that of 1D9.

Another aspect of the invention is a method of identifying expression of a mammalian CCR2 or portion of the receptor by a cell. According to the method, a composition comprising a cell or fraction thereof (e.g., a membrane fraction) is contacted with an antibody or functional fragment thereof (e.g., 1D9 or 8G2) which binds to a mammalian CCR2 protein or portion of the receptor under conditions appropriate for binding of the antibody thereto, and the formation of a complex between said antibody or fragment and said protein or portion thereof is detected. Detection of the complex, directly or indirectly, indicates the presence of the receptor on the cell. The present invention also relates to a kit for use in detecting the presence of CCR2 or a portion thereof in a biological sample, comprising an antibody or functional fragment thereof which binds to a mammalian CC-chemokine receptor 2 or a portion of said receptor, and one or more ancillary reagents suitable for detecting the presence of a complex between said antibody or fragment and said protein or portion thereof.

Also encompassed by the present invention are methods of identifying additional ligands or other substances which bind a mammalian CCR2 protein, including inhibitors and/ or promoters of mammalian CCR2 function. For example, agents having the same or a similar binding specificity as that of an antibody of the present invention or functional fragment thereof can be identified by a competition assay with said antibody or fragment. Thus, the present invention also encompasses methods of identifying ligands or other substances which bind the CCR2 receptor, including inhibitors (e.g., antagonists) or promoters (e.g., agonists) of receptor function. In one embodiment, cells which naturally express CCR2 receptor protein or suitable host cells which have been engineered to express a CCR2 receptor or variant encoded by a nucleic acid introduced into said cells are used in an assay to identify and assess the efficacy of ligands, inhibitors or promoters of receptor function. Such cells are also useful in assessing the function of the expressed receptor protein or polypeptide.

Thus, the invention also relates to a method of detecting or identifying an agent which binds a mammalian CCR2 or ligand binding variant thereof, comprising combining an agent to be tested, an antibody or antigen-binding fragment of the present invention (e.g., monoclonal antibody 1D9, an antibody having an epitopic specificity which is the same as or similar to that of 1D9, antigen-binding fragments of 1D9, monoclonal antibody 8G2, an antibody having an epitopic specificity which is the same as or similar to that of 8G2, and antigen-binding fragments of 8G2) and a composition comprising a mammalian CCR2 protein or a ligand binding variant thereof. The foregoing components can be combined under conditions suitable for binding of the antibody or antigen-binding fragment to mammalian CCR2 protein or a ligand binding variant thereof, and binding of the antibody or fragment to the mammalian CCR2 protein or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian CCR2 protein or a ligand binding variant thereof can be a membrane fraction of a cell bearing recombinant CCR2 protein or ligand binding variant thereof. The antibody or fragment thereof can be labeled with a label such as a radioisotope, spin label, antigen label, enzyme label, fluorescent group and chemiluminescent group. These and similar assays can be used to detect agents, including ligands (e.g., chemokines which interact with CCR2) or other substances, including inhibitors or promoters of receptor function, which can bind CCR2 and compete with the antibodies described herein for binding to the receptor.

According to the present invention, ligands, inhibitors or promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. The present invention also provides a method of treating inflammatory diseases, autoimmune diseases, atherosclerosis, and graft rejection, or HIV infection, comprising administering an inhibitor of receptor function (e.g., chemokine binding or HIV binding) to an individual (e.g., a mammal, such as a human). The present invention further provides a method of stimulating receptor function by administering a novel ligand or promoter to an individual, providing a new approach to selective stimulation of leukocyte function, which is useful, for example, in the treatment of infectious diseases and cancer.

Another aspect of the invention relates to a method of inhibiting HIV infection of a cell which expresses a mammalian CCR2 or portion thereof, comprising contacting the cell with an effective amount of an antibody or functional fragment thereof which binds to a mammalian CCR2 or portion of the receptor and inhibits HIV binding and infection. In a particular embodiment of the invention, the antibody or functional fragment thereof is any of 1D9, an antibody having an epitopic specificity which is the same as or similar to that of 1D9, an antibody which can compete with 1D9 for binding to human CCR2, and antigen-binding fragments thereof.

Also encompassed by the present invention is a method of inhibiting (e.g., treating) HIV in a patient, comprising administering to the patient an effective amount of an antibody or functional fragment thereof which binds to a mammalian CCR2 or a portion of said receptor and inhibits HIV binding to the CCR2 receptor. The anti-CCR2 antibody or fragment can be administered alone or in combination with one or more additional therapeutic agents, e.g., one or more antibodies which bind a co-receptor for HIV infection and inhibit binding to said co-receptor, such as an anti-CCR3, anti-CCR5, and/or anti-CXCR4 antibody.

Another aspect of the invention also relates to a method of preventing or inhibiting HIV infection in an individual, comprising administering to the individual an effective amount of an antibody or functional fragment thereof which binds to CCR2 and inhibits HIV binding to CCR2. According to the method, preventing HIV infection includes treatment in order to prevent (reduce or eliminate) infection of new cells in an infected individual or in order to prevent infection in an individual who may be, may have been or has been exposed to HIV. For example, individuals such as an HIV infected individual, a fetus of an HIV infected female, or a health care worker can be treated according to the method of the present invention.

The present invention also encompasses a method of inhibiting leukocyte trafficking in a patient, comprising administering to the patient an effective amount of an antibody or functional fragment thereof which binds to a mammalian CCR2 or portion of said receptor and inhibits function associated with binding of a ligand to the receptor.

The present invention also relates to a method of inhibiting or treating CCR2-mediated disorders, such as inflammatory disorders, comprising administering to a patient an effective amount of an antibody or functional fragment thereof which binds to a mammalian CCR2 or portion of said receptor and inhibits CCR2-mediated function. For example, the invention relates to a method of inhibiting or treating stenosis or restenosis of the vasculature comprising administering to a patient an effective amount of an antibody or functional fragment thereof which binds to a mammalian CCR2 or portion of said receptor and inhibits CCR2-mediated function.

The present invention further relates to an antibody or fragment thereof as described herein (e.g., monoclonal antibody 1D9 or an antigen-binding fragment thereof) for use in therapy (including prophylaxis) or diagnosis, and to the use of such an antibody or fragment for the manufacture of a medicament for the treatment of a CCR2-mediated disorder, or other disease or inflammatory condition as described herein.

BRIEF DESCRIPTION OF THE FIGURES

FIGS. 2A–2L FACS dot plots showing expression of CCR2 on most monocytes, a subpopulation of lymphocytes and a small subset of granulocytes. Whole blood cells were stained with one of three anti-CCR2 mAbs (5A11, generated using a peptide consisting of the first 32 amino acids of the CCR2 amino-terminus as an immunogen, and 1D9 and 8G2 generated as described herein using CCR2b L1/2 cell transfectants as the immunogen). Staining was analyzed by flow cytometry, and the lymphocyte, granulocyte and monocyte populations were gated using the forward and side light scatter. The X-axis represents forward light scatter (a measure of cell size), and the Y-axis fluorescence intensity of staining for CCR2. The level of negative control staining is indicated by a line.

FIG. 6A shows the results of chemotaxis assays of PBMC to 10 nM MCP-1 with no antibody, or 0.1 or 10 μg/ml of 1D9 or nonspecific murine IgG2a. The spontaneous nonspecific migration is also indicated.

FIG. 6B shows the results of chemotaxis assays of PBMC to 10 nM RANTES with no antibody, 10 μg/ml 1D9 or 10 μg/ml nonspecific murine IgG2a. The spontaneous nonspecific migration in the absence of RANTES is also indicated.

DETAILED DESCRIPTION OF THE INVENTION

Figure 1A:
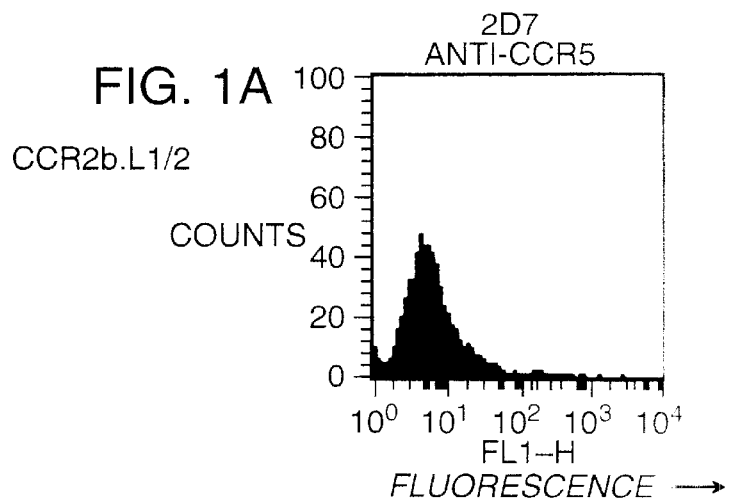
FIGS. 1A–1O fluorescence activated cell scanning (FACS) histogram profiles illustrating that mAbs 1D9 and 8G2 stain CCR2 transfectants but not CCR5 or CCR1 transfectants. L1/2 (also referred to herein as L1.2) murine pre-B lymphoma host cells were transfected with CCR2, CCR5 and CCR1 as indicated, and stained with antibodies with different receptor specificities. Staining was analyzed by flow cytometry.
Figure 1B:
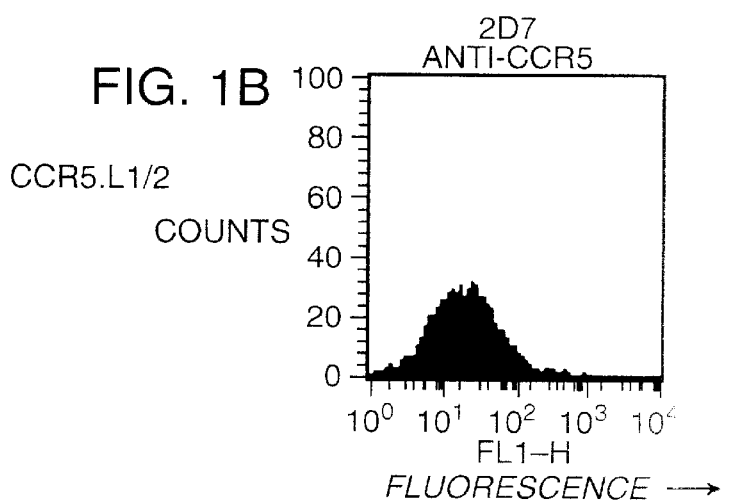
Figure 1C:
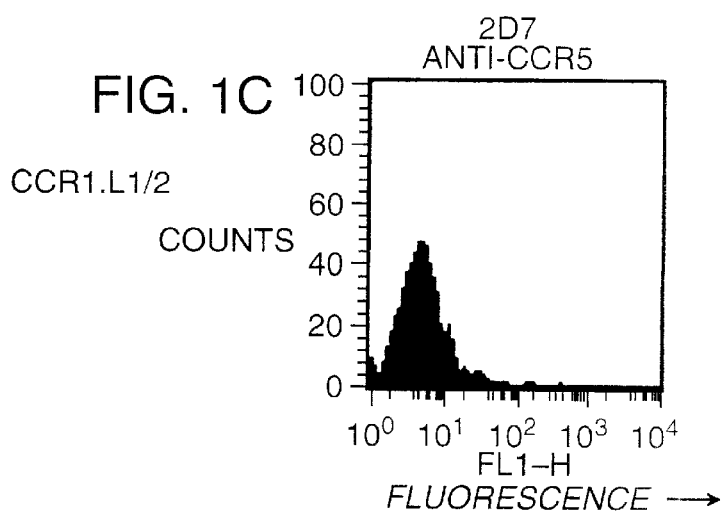
Figure 1D:
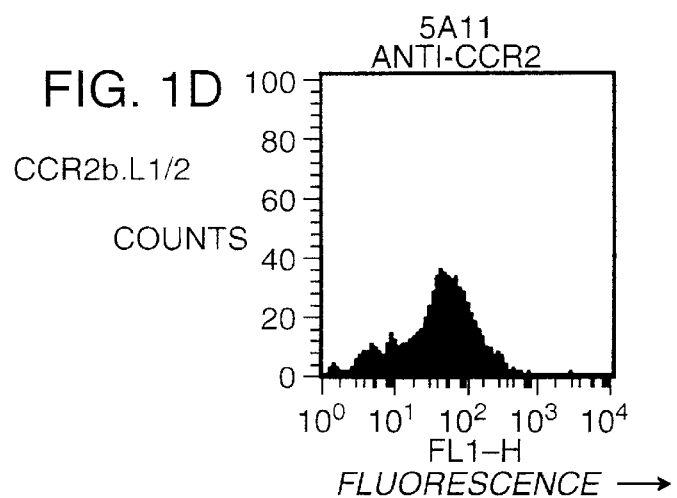
Figure 1E:
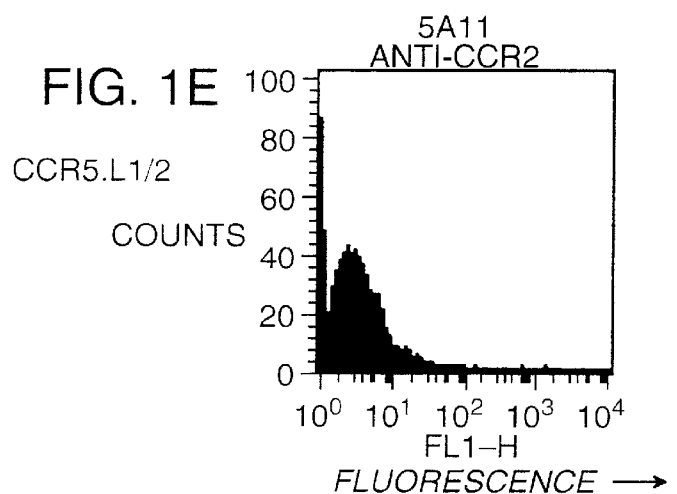
Figure 1F:
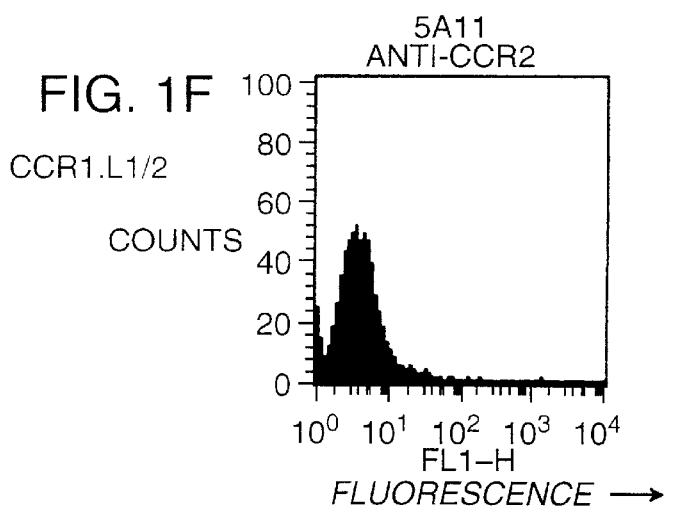
Figure 1G:
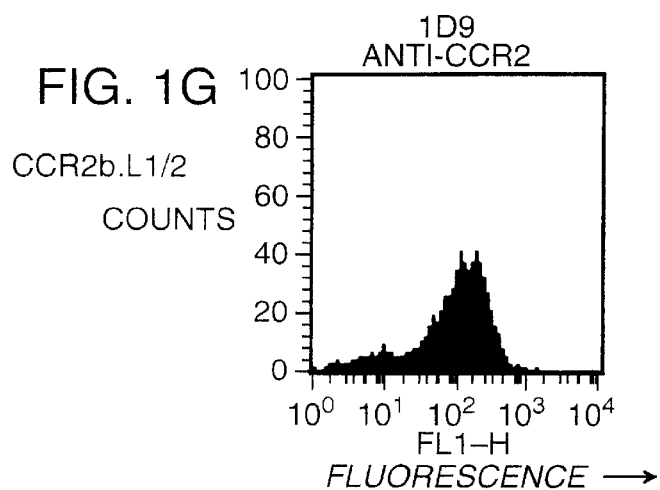
Figure 1H:
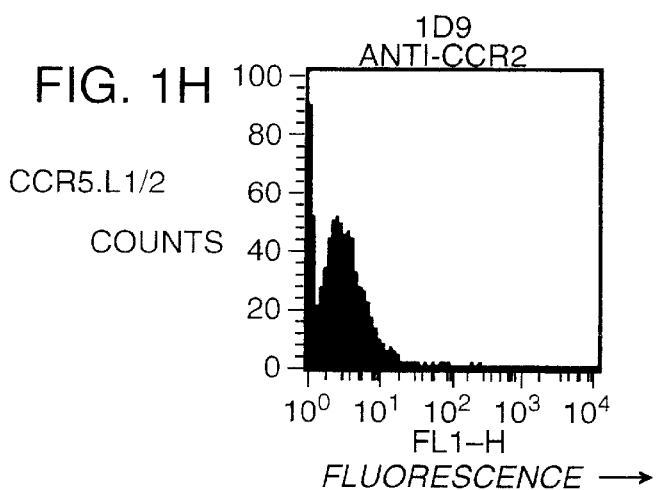
Figure 1I:
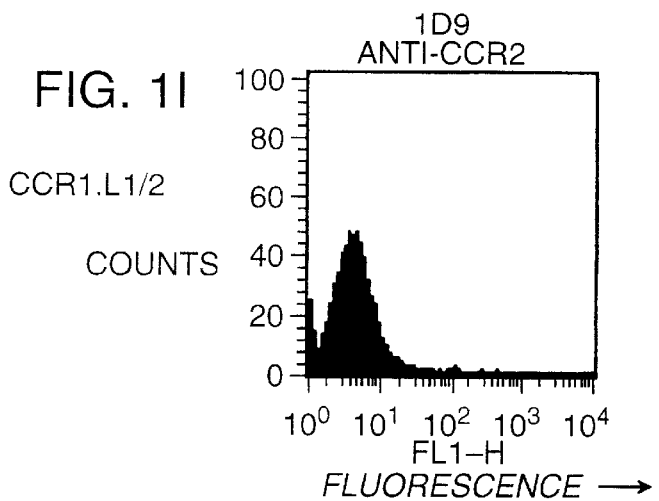
Figure 1J:
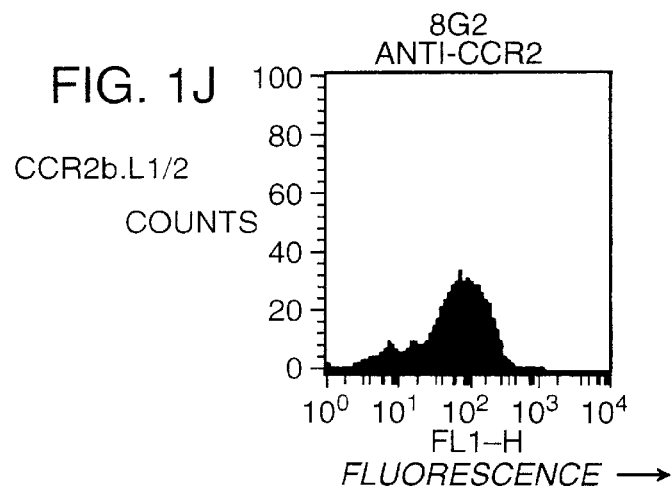
Figure 1K:
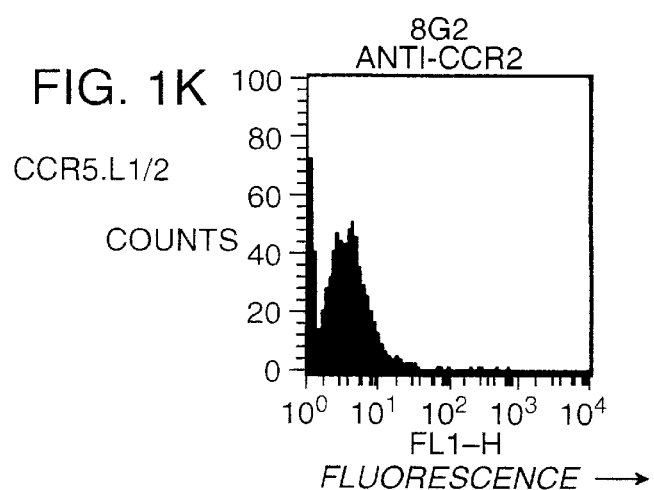
Figure 1L:
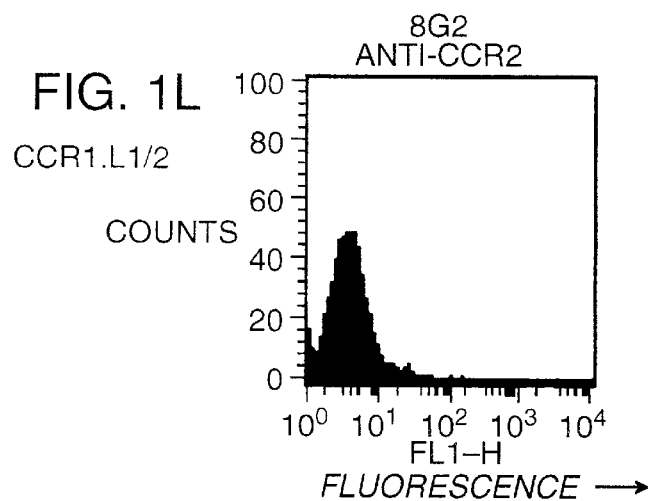
Figure 1M:
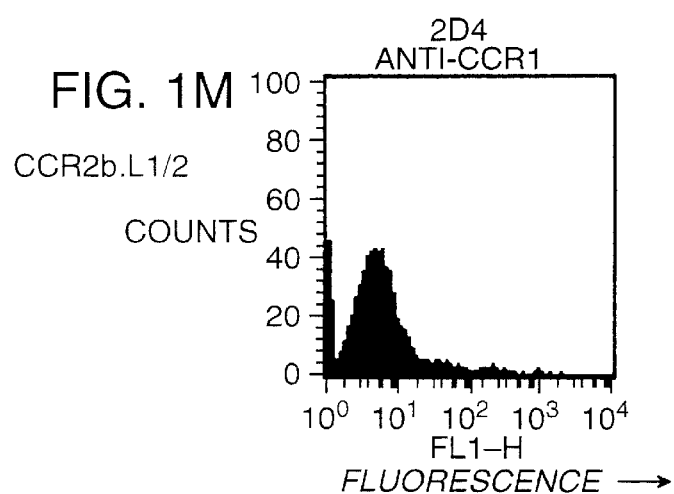
Figure 1N:
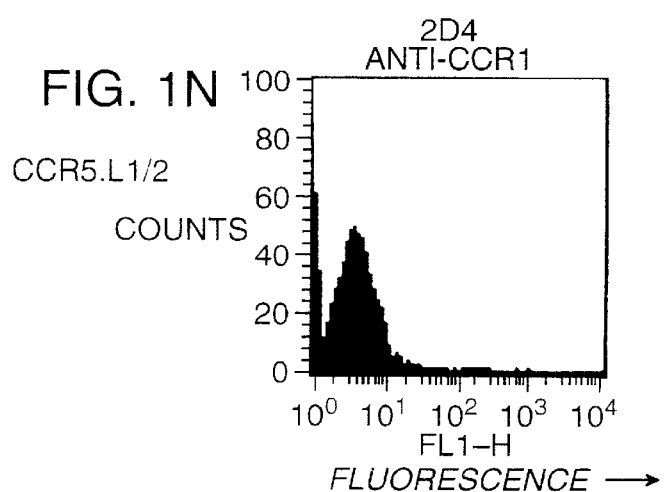

The present invention relates to an antibody (anti-CCR2) or functional fragment thereof which binds mammalian CC-chemokine receptor 2 (CCR2, CKR-2, MCP-1RA or MCP-1RB) or a portion of CCR2. In one embodiment, the antibody has specificity for human or rhesus CCR2 or portion thereof. In one embodiment, the antibodies (immunoglobulins) are raised against an isolated and/or recombinant mammalian CCR2 or portion thereof (e.g., peptide) or against a host cell which expresses mammalian CCR2. In a preferred embodiment, the antibodies specifically bind human CCR2 receptor(s) (e.g., CCR2a and/or CCR2b) or a portion thereof, and in a particularly preferred embodiment the antibodies have specificity for a naturally occurring or endogenous human CCR2. As used herein, "CC-chemokine receptor 2" ("CCR2") refers to CC-chemokine receptor 2a and/or CC-chemokine receptor 2b. Antibodies or functional fragments thereof which can inhibit one or more functions characteristic of a mammalian CCR2, such as a binding activity (e.g., ligand, inhibitor and/or promoter binding), a signaling activity (e.g., activation of a mammalian G protein, induction of a rapid and transient increase in the concentration of cytosolic free calcium [$Ca^{2+}$]i), and/or stimulation of a cellular response (e.g., stimulation of chemotaxis, exocytosis or inflammatory mediator release by leukocytes, integrin activation) are also encompassed by the present invention, such as an antibody which can inhibit binding of a ligand (i.e., one or more ligands) to CCR2 and/or one or more functions mediated by CCR2 in response to a ligand. For example, in one aspect, the antibodies or functional fragments thereof can inhibit (reduce or prevent) the interaction of receptor with a natural ligand, such as MCP-1, MCP-2, MCP-3 and/or MCP-4. In another aspect, an antibody or functional fragment thereof that binds to CCR2 can inhibit binding of MCP-1, MCP-2, MCP-3 and/or MCP-4 and/or HIV to mammalian CCR2 (e.g., human CCR2, non-human primate CCR2, murine CCR2). The antibodies or functional fragments thereof of the present invention can inhibit functions mediated by human CCR2, including leukocyte trafficking, HIV entry into a cell, T cell activation, inflammatory mediator release and/or leukocyte degranulation. Preferably, the antibodies or fragments can bind CCR2 with an affinity of at least about $0.1\times10^{-9}$ M, preferably at least about $1\times10^{-9}$ M, and more preferably at least about $3\times10^{-9}$ M. In a particular embodiment, antibodies or functional fragments thereof demonstrate inhibition of chemokine-induced (e.g., MCP-1-induced) chemotaxis of cells (e.g., PBMC) at less than about 150 μg/ml, preferably less than about 100 μg/ml, more preferably less than about 50 μg/ml, and even more preferably less than about 20 μg/ml.

In a further embodiment of the invention, the antibodies or functional fragments thereof of the invention can inhibit binding of a CCR2 ligand (e.g., a chemokine) to CCR2 with an $IC_{50}$ of less than about 1.0 μg/ml, preferably less than about 0.05 μg/ml, and more preferably less than about 0.005 μg/ml.

Murine monoclonal antibodies specific for CCR2, designated 1D9 and 8G2, were produced as described herein. In a preferred embodiment, the antibodies of the present invention bind human CCR2, and have an epitopic specificity which is the same as or similar to that of murine 1D9 or 8G2 antibody described herein. Antibodies with an epitopic specificity which is the same as or similar to that of murine 1D9 monoclonal antibody can be identified by their ability to compete with murine 1D9 monoclonal antibody for binding to human CCR2 (e.g., to cells bearing human CCR2, such as transfectants bearing CCR2, CD8+ cells, CD4+ cells, CDR45RO+ cells, CD25+ cells, monocytes, dendritic cells, macrophages and basophils). Similarly, antibodies with an epitopic specificity which is the same as or similar to that of murine 8G2 monoclonal antibody can be identified by their ability to compete with murine 8G2 monoclonal antibody for binding to human CCR2. Using receptor chimeras (Rucker et al., *Cell* 87:437–446 (1996)), the binding site of mAbs 1D9 and 8G2 has been mapped to the amino-terminal domain of human CC-chemokine receptor 2, specifically to an epitope comprising from about amino acid 1 to about amino acid 30 of the protein. Using these or other suitable techniques, antibodies having an epitopic specificity which is the same as or similar to that of an antibody of the present invention can be identified. mAbs 1D9 and 8G2 have epitopic specificity for the amino-terminal domain of the CCR2 receptor, e.g., from about amino acid number 1 to about amino acid number 30 of the receptor protein. Thus, the invention pertains to an antibody or functional portion thereof which binds to the amino-terminal domain or portion thereof of mammalian CC-chemokine receptor 2, and particularly to an epitope comprising from about amino acid 1 to about amino acid 30 of mammalian CC-chemokine receptor 2.

The invention also relates to a bispecific antibody, or functional fragment thereof (e.g., F(ab')$_2$), which has the same or similar epitopic specificity as at least two of the antibodies described herein (see, e.g., U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.). For example, a bispecific antibody of the present invention can have the same or similar epitopic specificity as mAb 1D9 and 8G2, e.g., binds the amino terminal domain, or portion thereof, of mammalian CCR2 protein.

Hybridoma cell lines producing antibodies according to the present invention were deposited on Jul. 17, 1998, on behalf of LeukoSite, Inc., 215 First Street, Cambridge, Mass. 02142, U.S.A., at the American Type Culture Collection, 10801 University Boulevard, Manassas, Va. 20110, U.S.A., under Accession Nos. HB-12549 (1D9) and HB-12550 (8G2). The present invention also pertains to the hybridoma cell lines deposited under ATCC Accession No. HB-12549 and ATCC Accession No. HB-12550, as well as to the monoclonal antibodies produced by the hybridoma cell lines deposited under ATCC Accession Nos. HB-12549 and HB-12550.

The antibodies of the present invention can be polyclonal or monoclonal, and the term "antibody" is intended to encompass both polyclonal and monoclonal antibodies. Furthermore, it is understood that methods described herein which utilize 8G2 can also utilize functional fragments (e.g., antigen-binding fragments) of 8G2, antibodies which have the same or similar epitopic specificity as 8G2, and combinations thereof, optionally in combination with antibodies or fragments having an epitopic specificity which is not the same as or similar to 8G2; similarly, methods described as utilizing 1D9 can also utilize functional fragments of 1D9, antibodies which have the same or similar epitopic specificity as 1D9, and combinations thereof, optionally in combination with antibodies or fragments having an epitopic specificity which is not the same as or similar to 1D9. Antibodies of the present invention can be raised against an appropriate immunogen, such as isolated and/or recombinant mammalian CCR2 protein or portion thereof, or synthetic molecules, such as synthetic peptides. In a preferred embodiment, cells which express receptor, such as transfected cells, can be used as immunogens or in a screen for antibody which binds receptor.

The antibodies of the present invention, and fragments thereof, are useful in therapeutic, diagnostic and research applications as described herein. The present invention encompasses an antibody or functional portion thereof of the present invention (e.g., mAb 1D9 or 8G2, or antigen-binding fragments thereof) for use in therapy (including prophylaxis) or diagnosis (e.g., of particular diseases or conditions as described herein), and use of such antibodies or functional portions thereof for the manufacture of a medicament for use in treatment of diseases or conditions as described herein.

Preparation of immunizing antigen, and polyclonal and monoclonal antibody production can be performed as described herein, or using other suitable techniques. A variety of methods have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology,* Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) can be isolated using selective culture conditions, and cloned by limiting dilution. Cells which produce antibodies with the desired binding properties can be selected by a suitable assay (e.g., ELISA).

Other suitable methods of producing or isolating antibodies which bind CCR2, including human or artificial antibodies, can be used, including, for example, methods which select recombinant antibody (e.g., single chain Fv or Fab) from a library, or which rely upon immunization of transgenic animals (e.g., mice) capable of producing a repertoire of human antibodies (see e.g., Jakobovits et al., *Proc. Natl. Acad. Sci. USA,* 90: 2551–2555 (1993); Jakobovits et al., *Nature,* 362: 255–258 (1993); Lonberg et al., U.S. Pat. No. 5,545,806; Surani et al., U.S. Pat. No. 5,545,807).

Single chain antibodies, and chimeric, humanized or primatized (CDR-grafted) antibodies, as well as chimeric or CDR-grafted single chain antibodies, and the like, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; and Queen et al., U.S. Pat. Nos. 5,585,089, 5,698,761 and 5,698,762. See also, Newman, R. et al., *BioTechnology,* 10: 1455–1460 (1992), regarding primatized antibody, and Ladner et al., U.S. Pat. No. 4,946,778 and Bird, R. E. et al., *Science,* 242: 423–426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function and/or modulation function of the full-length antibody from which they are derived. Preferred functional fragments retain an antigen-binding function of a corresponding full-length antibody (e.g., the ability to bind a mammalian CCR2). Particularly preferred functional fragments retain the ability to inhibit one or more functions characteristic of a mammalian CCR2, such as a binding activity, a signaling activity, and/or stimulation of a cellular response. For example, in one embodiment, a functional fragment can inhibit the interaction of CCR2 with one or more of its ligands (e.g., MCP-1, MCP-2, MCP-3 and/or MCP-4) and/or can inhibit one or more receptor-mediated functions, such as leukocyte trafficking, HIV entry into cells, T cell activation, inflammatory mediator release and/or leukocyte degranulation.

For example, antibody fragments capable of binding to a mammalian CCR2 receptor or portion thereof, including, but not limited to, Fv, Fab, Fab' and $F(ab')_2$ fragments are encompassed by the invention. Such fragments can be produced by enzymatic cleavage or by recombinant techniques, for example. For instance, papain or pepsin cleavage can generate Fab or $F(ab')_2$ fragments, respectively. Antibodies can also be produced in a variety of truncated forms using antibody genes in which one or more stop codons has been introduced upstream of the natural stop site. For example, a chimeric gene encoding a $F(ab')_2$ heavy chain portion can be designed to include DNA sequences encoding the $CH_1$ domain and hinge region of the heavy chain.

The term "humanized immunoglobulin" as used herein refers to an immunoglobulin comprising portions of immunoglobulins of different origin, wherein at least one portion is of human origin. Accordingly, the present invention relates to a humanized immunoglobulin which binds mammalian CCR2 (e.g., human CCR2, murine CCR2), said immunoglobulin comprising an antigen-binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one embodiment, the humanized immunoglobulin can compete with murine 1D9 or 8G2 monoclonal antibody for binding to human CCR2. In a preferred embodiment, the antigen-binding region of the humanized immunoglobulin (a) is derived from 1D9 monoclonal antibody (e.g., as in a humanized immunoglobulin comprising CDR1, CDR2 and CDR3 of the 1D9 light chain and CDR1, CDR2 and CDR3 of the 1D9 heavy chain) or (b) is derived from 8G2 monoclonal antibody (e.g., as in a humanized immunoglobulin comprising CDR1, CDR2 and CDR3 of the 8G2 light chain and CDR1, CDR2 and CDR3 of the 8G2 heavy chain). Chimeric or CDR-grafted single chain antibodies are also encompassed by the term humanized immunoglobulin.

Such humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., *Nucl. Acids Res.,* 17: 5404 (1989)); Sato, K., et al., *Cancer Research,* 53: 851–856 (1993); Daugherty, B. L. et al., *Nucleic Acids Res.,* 19(9): 2471–2476 (1991); and Lewis, A. P. and J. S. Crowe, *Gene,* 101: 297–302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

Anti-idiotypic antibodies are also provided. Anti-idiotypic antibodies recognize antigenic determinants associated with the antigen-binding site of another antibody. Anti-idiotypic antibodies can be prepared against second antibody by immunizing an animal of the same species, and preferably of the same strain, as the animal used to produce the second antibody. See e.g., U.S. Pat. No. 4,699,880.

The present invention also pertains to the hybridoma cell lines deposited under ATCC Accession Nos. HB-12549 and HB-12550, as well as to the monoclonal antibodies produced by the hybridoma cell lines deposited under ATCC Accession Nos. HB-12549 and HB-12550. The cell lines of the present invention have uses other than for the production of the monoclonal antibodies. For example, the cell lines of the present invention can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-CCR2 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-CCR2 light or heavy chain can be isolated (e.g., by PCR) or cDNA libraries can be prepared from mRNA isolated from the cell lines, and cDNA clones encoding an anti-CCR2 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome). For production, host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host cells, medium, milk). It will be appreciated that the method of production encompasses expression in a host cell of a transgenic animal (see e.g., WO 92/03918, GenPharm International, published Mar. 19, 1992).

As described herein, antibodies and functional fragments thereof of the present invention can block (inhibit) binding of a ligand to CCR2 and/or inhibit function associated with binding of the ligand to the CCR2. As discussed below various methods can be used to assess inhibition of binding of a ligand to CCR2 and/or function associated with binding of the ligand to the receptor.

Binding Assays

As used herein "mammalian CCR2 protein" refers to naturally occurring or endogenous mammalian CCR2 proteins and to proteins having an amino acid sequence which is the same as that of a naturally occurring or endogenous corresponding mammalian CCR2 protein (e.g., recombinant proteins). Accordingly, as defined herein, the term includes mature receptor protein, polymorphic or allelic variants, and other isoforms of a mammalian CCR2 (e.g., produced by alternative splicing or other cellular processes), and modified or unmodified forms of the foregoing (e.g., glycosylated, unglycosylated). Mammalian CCR2 proteins can be isolated and/or recombinant proteins (including synthetically produced proteins). Naturally occurring or endogenous mammalian CCR2 proteins include wild type proteins such as mature CCR2, polymorphic or allelic variants and other isoforms which occur naturally in mammals (e.g., humans, non-human primates), such as the CCR2 a and CCR2 b forms of the receptor protein which are produced by alternative splicing of the carboxy-terminus of the protein. Such proteins can be recovered or isolated from a source which naturally produces mammalian CCR2, for example. These proteins and mammalian CCR2 proteins having the same amino acid sequence as a naturally occurring or endogenous corresponding mammalian CCR2, are referred to by the name of the corresponding mammal. For example, where the corresponding mammal is a human, the protein is designated as a human CCR2 protein (e.g., a recombinant human CCR2 produced in a suitable host cell).

"Functional variants" of mammalian CCR2 proteins include functional fragments, functional mutant proteins, and/or functional fusion proteins (e.g., produced via mutagenesis and/or recombinant techniques). Generally, fragments or portions of mammalian CCR2 proteins include those having a deletion (i.e., one or more deletions) of an amino acid (i.e., one or more amino acids) relative to the mature mammalian CCR2 protein (such as N-terminal, C-terminal or internal deletions). Fragments or portions in which only contiguous amino acids have been deleted or in which non-contiguous amino acids have been deleted relative to mature mammalian CCR2 protein are also envisioned.

Generally, mutants of mammalian CCR2 proteins include natural or artificial variants of a mammalian CCR2 protein differing by the addition, deletion and/or substitution of one or more contiguous or non-contiguous amino acid residues (e.g., receptor chimeras). Such mutations can be in a conserved region or nonconserved region (compared to other CXC and/or CC chemokine receptors), extracellular, cytoplasmic, or transmembrane region, for example.

Generally, fusion proteins encompass polypeptides comprising a mammalian CCR2 (e.g., human CCR2) as a first moiety, linked via a peptide cond to a second moiety not occurring in the mammalian CCR2 as found in nature. Thus, the second moiety can be an amino acid, oligopeptide or polypeptide. The first moiety can be in an N-terminal location, C-terminal location or internal to the fusion protein. In one embodiment, the fusion protein comprises an affinity ligand (e.g., an enzyme, an antigen, epitope tage) as the first moiety, and a second moiety comprising a linker sequence and human CCR2 or a portion thereof.

A "functional fragment or portion", "functional mutant" and/or "functional fusion protein" of a mammalian CCR2 protein refers to an isolated and/or recombinant protein or polypeptide which has at least one function characteristic of a mammalian CCR2 protein as described herein, such as a binding activity, a signaling activity and/or ability to stimulate a cellular response. Preferred functional variants can bind a ligand (i.e., one or more ligands such as MCP-1, MCP-2, MCP-3 and/or MCP-4), and are referred to herein as "ligand binding variants".

In one embodiment, a functional variant of mammalian CCR2 shares at least about 85% sequence identity with said mammalian CCR2, preferably at least about 90% sequence identity, and more preferably at least about 95% sequence identity with said mammalian CCR2. The nucleic acid and amino acid sequences of human CCR2a and CCR2b are described in U.S. Pat. No. 5,707,815. Sequence identity can be determine using a suitable program, such as the Blastx program (Version 1.4), using appropriate parameters, such as default parameters. In one embodiment, parameters for Blastx search are scoring matrix BLOSUM62, W=3. In another embodiment, a functional variant comprises a nucleic acid sequence which is different from the naturally-occurring nucleic acid molecule but which, due to the degeneracy of the genetic code, encodes mammalian CCR2 or a portion thereof.

A composition comprising an isolated and/or recombinant mammalian CCR2 or functional variant thereof can be maintained under conditions suitable for binding, the mammalian CCR2 or variant is contacted with an antibody or fragment to be tested, and binding is detected or measured directly or indirectly. In one embodiment, cells which naturally express CCR2 or cells comprising a recombinant nucleic acid sequence which encodes a mammalian CCR2 or variant thereof are used. The cells are maintained under conditions appropriate for expression of receptor. The cells are contacted with an antibody or fragment under conditions suitable for binding (e.g., in a suitable binding buffer), and binding is detected by standard techniques. To determine binding, the extent of binding an be determined relative to a suitable control (e.g., compared with background determined in the absence of antibody, compared with binding of a second antibody (i.e., a standard), compared with binding of antibody to untransfected cells). A cellular fraction, such as a membrane fraction, containing receptor or liposomes comprising receptor can be used in lieu of whole cells.

In one embodiment, the antibody is labeled with a suitable label (e.g., fluorescent label, isotope label, antigen or epitope label, enzyme label), and binding is determined by detection of the label. In another embodiment, bound antibody can be detected by labeled second antibody. Specificity of binding can be assessed by competition or displacement, for example, using unlabeled antibody or a ligand as competitor.

Binding inhibition assays can also be used to identify antibodies or fragments thereof which bind CCR2 and inhibit binding of another compound such as a ligand (e.g., MCP-1, MCP-2, MCP-3 and/or MCP-4) to CCR2 or a functional variant. For example, a binding assay can be conducted in which a reduction in the binding of a ligand of CCR2 (in the presence of an antibody), as compared to binding of the ligand in the absence of the antibody, is detected or measured. A composition comprising an isolated and/or recombinant mammalian CCR2 or functional variant thereof can be contacted with the ligand and antibody simultaneously, or one after the other, in either order. A reduction in the extent of binding of the ligand in the presence of the antibody, is indicative of inhibition of binding by the antibody. For example, binding of the ligand could be decreased or abolished.

In one embodiment, direct inhibition of the binding of a ligand (e.g., a chemokine such as MCP-1) to a mammalian CCR2 or variant thereof by an antibody or fragment is monitored. For example, the ability of an antibody to inhibit the binding of $^{125}$I-labeled MCP-1, $^{125}$I-labeled MCP-2, $^{125}$I-labeled MCP-3 or $^{125}$I-labeled MCP-4 to mammalian CCR2 can be monitored. Such an assay can be conducted using suitable cells bearing CCR2 or a functional variant thereof, such as isolated blood cells (e.g., T cells, PBMC) or a suitable cell line naturally expressing CCR2, or a cell line containing nucleic acid encoding a mammalian CCR2, or a membrane fraction from said cells, for instance.

Other methods of identifying the presence of an antibody which binds CCR2 are available, such as other suitable binding assays, or methods which monitor events which are triggered by receptor binding, including signaling function and/or stimulation of a cellular response (e.g., leukocyte trafficking).

It will be understood that the inhibitory effect of antibodies of the present invention can be assessed in a binding inhibition assay. Competition between antibodies for receptor binding can also be assessed in the method. Antibodies which are identified in this manner can be further assessed to determine whether, subsequent to binding, they act to inhibit other functions of CCR2 and/or to assess their therapeutic utility.

Signaling Assays

The binding of a ligand or promoter, such as an agonist, to CCR2 can result in signaling by this G protein-coupled receptor, and the activity of G proteins as well as other intracellular signaling molecules is stimulated. The induction of signaling function by a compound (e.g., an antibody or fragment thereof) can be monitored using any suitable method. Such an assay can be used to identify antibody agonists of CCR2. The inhibitory activity of an antibody or functional fragment thereof can be determined using a ligand or promoter in the assay, and assessing the ability of the antibody to inhibit the activity induced by ligand or promoter.

G protein activity, such as hydrolysis of GTP to GDP, or later signaling events triggered by receptor binding, such as induction of rapid and transient increase in the concentration of intracellular (cytosolic) free calcium $[Ca^{2+}]i$, can be assayed by methods known in the art or other suitable methods (see e.g., Neote, K. et al., *Cell,* 72: 415–425 1993); Van Riper et al., *J. Exp. Med.,* 177: 851–856 (1993); Dahinden, C. A. et al., *J. Exp. Med.,* 179: 751–756 (1994)).

For example, the functional assay of Sledziewski et al. using hybrid G protein coupled receptors can be used to monitor the ability a ligand or promoter to bind receptor and activate a G protein (Sledziewski et al., U.S. Pat. No. 5,284,746, the teachings of which are incorporated herein by reference).

Such assays can be performed in the presence of the antibody or fragment thereof to be assessed, and the ability of the antibody or fragment to inhibit the activity induced by the ligand or promoter is determined using known methods and/or methods described herein.

Chemotaxis and Assays of Cellular Stimulation

Chemotaxis assays can also be used to assess the ability of an antibody or functional fragment thereof to block binding of a ligand to mammalian CCR2 or functional variant thereof and/or inhibit function associated with binding of the ligand to the receptor. These assays are based on the functional migration of cells in vitro or in vivo induced by a compound. Chemotaxis can be assessed as described in the Examples, e.g., in an assay utilizing a 96-well chemotaxis plate, or using other art-recognized methods for assessing chemotaxis. For example, the use of an in vitro transendothelial chemotaxis assay is described by Springer et al. (Springer et al., WO 94/202, published Sep. 15, 1994, the teachings of which are incorporated herein by reference; see also Berman et al., *Immunol. Invest.* 17: 625–677 (1988)). Migration across endothelium into collagen gels has also been described (Kavanaugh et al., *J. Immunol.,* 146:

4149–4156 (1991)). Stable transfectants of mouse L1-2 pre-B cells or of other suitable host cells capable of chemotaxis can be used in chemotaxis assays, for example.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen. Such assays provide an in vitro approximation of leukocyte "homing".

For example, one can detect or measure inhibition of the migration of cells in a suitable container (a containing means), from a first chamber into or through a microporous membrane into a second chamber which contains an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3–8 microns, and preferably about 5–8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody or fragment by determining the presence of the label adherent to the membrane and/or present in the second chamber using an appropriate method (e.g., by detecting radioactivity, fluorescence, immunoassay). The extent of migration induced by an antibody agonist can be determined relative to a suitable control (e.g., compared to background migration determined in the absence of the antibody, compared to the extent of migration induced by a second compound (i.e., a standard), compared with migration of untransfected cells induced by the antibody).

In one embodiment, particularly for T cells, monocytes or cells expressing a mammalian CCR2, transendothelial migration can be monitored. In this embodiment, transmigration through an endothelial cell layer is assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (Clonetics Corp, San Diego, Calif.). To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of a compound, from a first surface of the filter toward an opposite second surface of the filter, wherein the filter contains an endothelial cell layer on a first surface. Directional migration occurs from the area adjacent to the first surface, into or through the membrane, towards a compound situated on the opposite side of the filter. The concentration of compound present in the area adjacent to the second surface, is greater than that in the area adjacent to the first surface.

In one embodiment used to test for an antibody inhibitor, a composition comprising cells capable of migration and expressing a mammalian CCR2 receptor can be placed in the first chamber. A composition comprising one or more ligands or promoters capable of inducing chemotaxis of the cells in the first chamber (having chemoattractant function) is placed in the second chamber. Preferably shortly before the cells are placed in the first chamber, or simultaneously with the cells, a composition comprising the antibody to be tested is placed, preferably, in the first chamber. Antibodies or functional fragments thereof which can bind receptor and inhibit the induction of chemotaxis, by a ligand or promoter, of the cells expressing a mammalian CCR2 in this assay are inhibitors of receptor function (e.g., inhibitors of stimulatory function). A reduction in the extent of migration induced by the ligand or promoter in the presence of the antibody or fragment is indicative of inhibitory activity. Separate binding studies (see above) could be performed to determine whether inhibition is a result of binding of the antibody to receptor or occurs via a different mechanism.

In vivo assays which monitor leukocyte infiltration of a tissue, in response to injection of a compound (e.g., chemokine or antibody) in the tissue, are described below (see Models of Inflammation). These models of in vivo homing measure the ability of cells to respond to a ligand or promoter by emigration and chemotaxis to a site of inflammation and to assess the ability of an antibody or fragment thereof to block this emigration.

In addition to the methods described, the effects of an antibody or fragment on the stimulatory function of CCR2 can be assessed by monitoring cellular responses induced by active receptor, using suitable host cells containing receptor.
Identification of Additional Ligands, Inhibitors and/or Promoters of Mammalian CCR2 Function The assays described above, which can be used to assess binding and function of the antibodies and fragments of the present invention, can be adapted to identify additional ligands or other substances which bind a mammalian CCR2 or functional variant thereof, as well as inhibitors and/or promoters of mammalian CCR2 function. For example, agents having the same or a similar binding specificity as that of an antibody of the present invention or functional portion thereof can be identified by a competition assay with said antibody or portion thereof. Thus, the present invention also encompasses methods of identifying ligands of the receptor or other substances which bind a mammalian CCR2 protein, as well as inhibitors (e.g., antagonists) or promoters (e.g., agonists) of receptor function. In one embodiment, cells bearing a mammalian CCR2 protein or functional variant thereof (e.g., leukocytes, cell lines or suitable host cells which have been engineered to express a mammalian CCR2 protein or functional variant encoded by a nucleic acid introduced into said cells) are used in an assay to identify and assess the efficacy of ligands or other substances which bind receptor, including inhibitors or promoters of receptor function. Such cells are also useful in assessing the function of the expressed receptor protein or polypeptide.

According to the present invention, ligands and other substances which bind receptor, inhibitors and promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. Thus, the present invention provides a method of treating inflammatory diseases, including autoimmune disease and graft rejection, comprising administering an inhibitor of receptor function to an individual (e.g., a mammal). The present invention further provides a method of stimulating receptor function by administering a novel ligand or promoter of receptor function to an individual, providing a new approach to selective stimulation of leukocyte function, which is useful, for example, in the treatment of infectious diseases and cancer.

As used herein, a "ligand" of a mammalian CCR2 protein refers to a particular class of substances which bind to a mammalian CCR2 protein, including natural ligands and synthetic and/or recombinant forms of natural ligands. Infectious agents having a tropism for mammalian CCR2 positive cells (e.g., viruses such as HIV) can also bind to a mammalian CCR2 protein. A natural ligand of a selected mammalian receptor is of a mammalian origin which is the same as that of the mammalian CCR2 protein (e.g., a chemokine such as MCP-1, MCP-2, MCP-3 and/or MCP-4). In a preferred embodiment, ligand binding of a mammalian CCR2 protein occurs with high affinity.

As used herein, an "inhibitor" is a substance which inhibits (decreases or prevents) at least one function characteristic of a mammalian CCR2 protein (e.g., a human CCR2), such as a binding activity (e.g., ligand binding, promoter binding, antibody binding), a signaling activity (e.g., activation of a mammalian G protein, induction of rapid and transient increase in the concentration of cytosolic free calcium $[Ca^{2+}]i$), and/or cellular response function (e.g., stimulation of chemotaxis, exocytosis or inflammatory mediator release by leukocytes). An inhibitor is also a substance which inhibits HIV entry into a cell. The term inhibitor refers to substances including antagonists which bind receptor (e.g., an antibody, a mutant of a natural ligand, small molecular weight organic molecules, other competitive inhibitors of ligand binding), and substances which inhibit receptor function without binding thereto (e.g., an anti-idiotypic antibody).

As used herein, a "promoter" is a substance which promotes (induces, causes, enhances or increases) at least one function characteristic of a mammalian CCR2 protein (e.g., a human CCR2), such as a binding activity (e.g., ligand, inhibitor and/or promoter binding), a signaling activity (e.g., activation of a mammalian G protein, induction of rapid and transient increase in the concentration of cytosolic free calcium $[Ca^{2+}]i$), and/or a cellular response function (e.g., stimulation of chemotaxis, exocytosis or inflammatory mediator release by leukocytes). The term promoter refers to substances including agonists which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

Thus, the invention also relates to a method of detecting or identifying an agent which binds a mammalian CC-chemokine receptor 2 or ligand binding variant thereof, including ligands, inhibitors, promoters, and other substances which bind a mammalian CCR2 receptor or functional variant. According to the method, an agent to be tested, an antibody or antigen-binding fragment of the present invention (e.g., 8G2, 1D9, an antibody having an epitopic specificity which is the same as or similar to that of 8G2 or 1D9, and antigen-binding fragments thereof) and a composition comprising a mammalian CC-chemokine receptor 2 or a ligand binding variant thereof can be combined. The foregoing components are combined under conditions suitable for binding of the antibody or antigen-binding fragment to mammalian CC-chemokine receptor 2 or a ligand binding variant thereof, and binding of the antibody or fragment to the mammalian CC-chemokine receptor 2 or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian CC-chemokine receptor 2 or a ligand binding variant thereof can be a membrane fraction of a cell bearing recombinant chemokine receptor 2 protein or ligand binding variant thereof. The antibody or fragment thereof can be labeled with a label such as a radioisotope, spin label, antigen or epitope label, enzyme label, fluorescent group and chemiluminescent group.

In one embodiment, the invention relates to a method of detecting or identifying an agent which binds a mammalian CC-chemokine receptor 2 or a ligand binding variant thereof, comprising combining an agent to be tested, an antibody or antigen-binding fragment of the present invention (e.g., 1D9, 8G2, an antibody having an epitopic specificity which is the same as or similar to that of 1D9 or 8G2, or antigen-binding fragments thereof) and a cell bearing a mammalian CC-chemokine receptor 2 or a ligand binding variant thereof. The foregoing components are combined under conditions suitable for binding of the antibody or antigen-binding fragment to the CCR2 protein or ligand binding variant thereof, and binding of the antibody or fragment to the mammalian CC-chemokine receptor 2 or variant is detected or measured, either directly or indirectly, by methods described herein and or other suitable methods. A decrease in the amount of complex formed relative to a suitable control is indicative that the agent binds the receptor or variant. The antibody or fragment thereof can be labeled with a label selected from the group consisting of a radioisotope, spin label, antigen or epitope label, enzyme label, fluorescent group and chemiluminescent group. These and similar assays can be used to detect agents, including ligands (e.g., chemokines or strains of HIV which interact with CCR2) or other substances, including inhibitors or promoters of receptor function, which can bind CCR2 and compete with the antibodies described herein for binding to the receptor.

The assays described above can be used, alone or in combination with each other or other suitable methods, to identify ligands or other substances which bind a mammalian CCR2 protein, and inhibitors or promoters of a mammalian CCR2 protein or variant. The in vitro methods of the present invention can be adapted for high-throughput screening in which large numbers of samples are processed (e.g., a 96-well format). Cells expressing mammalian CCR2 (e.g., human CCR2) at levels suitable for high-throughput screening can be used, and thus, are particularly valuable in the identification and/or isolation of ligands or other substances which bind receptor, and inhibitors or promoters of mammalian CCR2 proteins. Expression of receptor can be monitored in a variety of ways. For instance, expression can be monitored using antibodies of the present invention which bind receptor or a portion thereof. Also, commercially available antibodies can be used to detect expression of an antigen- or epitope-tagged fusion protein comprising a receptor protein or polypeptide (e.g., FLAG tagged receptors), and cells expressing the desired level can be selected.

Nucleic acid encoding a mammalian CCR2 protein or functional variant thereof can be incorporated into an expression system to produce a receptor protein or polypeptide. An isolated and/or recombinant mammalian CCR2 protein or variant, such as a receptor expressed in cells stably or transiently transfected with a construct comprising a recombinant nucleic acid encoding a mammalian CCR2 protein or variant, or in a cell fraction containing receptor (e.g., a membrane fraction from transfected cells, liposomes incorporating receptor), can be used in tests for receptor function. The receptor can be further purified if desired. Testing of receptor function can be carried out in vitro or in vivo.

An isolated and/or recombinant mammalian CCR2 protein or functional variant thereof, such as a human CCR2, can be used in the present method, in which the effect of a compound is assessed by monitoring receptor function as described herein or using other suitable techniques. For example, stable or transient transfectants (e.g., baculovirus infected Sf9 cells, stable tranfectants of mouse L1/2 pre-B cells), can be used in binding assays. Stable transfectants of Jurkat cells or of other suitable cells capable of chemotaxis can be used (e.g., mouse L1/2 pre-B cells) in chemotaxis assays, for example.

According to the method of the present invention, compounds can be individually screened or one or more compounds can be tested simultaneously according to the methods herein. Where a mixture of compounds is tested, the compounds selected by the processes described can be separated (as appropriate) and identified by suitable methods (e.g., PCR, sequencing, chromatography, mass spectroscopy). The presence of one or more compounds (e.g., a ligand, inhibitor, promoter) in a test sample can also be determined according to these methods.

Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.,* 37: 2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; Rutter, W. J. et al. U.S. Pat. No. 5,010,175; Huebner, V. D. et al., U.S. Pat. No. 5,182, 366; and Geysen, H. M., U.S. Pat. No. 4,833,092). Where compounds selected from a combinatorial library by the present method carry unique tags, identification of individual compounds by chromatographic methods is possible.

In one embodiment, phage display methodology is used. For example, a mammalian CCR2 protein or functional variant, an antibody or functional portion thereof of the present invention, and a phage (e.g., a phage or collection of phage such as a library) displaying a polypeptide, can be combined under conditions appropriate for binding of the antibody or portion thereof to the mammalian CCR2 protein or variant (e.g., in a suitable binding buffer). Phage which can compete with the antibody or portion thereof and bind to the mammalian CCR2 protein or variant can be detected or selected using standard techniques or other suitable methods. Bound phage can be separated from receptor using a suitable elution buffer. For example, a change in the ionic strength or pH can lead to a release of phage. Alternatively, the elution buffer can comprise a release component or components designed to disrupt binding of compounds (e.g., one or more compounds which can disrupt binding of the displayed peptide to the receptor, such as a ligand, inhibitor, and/or promoter which competitively inhibits binding). Optionally, the selection process can be repeated or another selection step can be used to further enrich for phage which bind receptor. The displayed polypeptide can be characterized (e.g., by sequencing phage DNA). The polypeptides identified can be produced and further tested for binding, and for inhibitor or promoter function. Analogs of such peptides can be produced which will have increased stability or other desirable properties.

In one embodiment, phage expressing and displaying fusion proteins comprising a coat protein with an N-terminal peptide encoded by random sequence nucleic acids can be produced. Suitable host cells expressing a mammalian CCR2 protein or variant and an anti-CCR2 antibody or functional portion thereof, are combined with the phage, bound phage are selected, recovered and characterized. (See e.g., Doorbar, J. and G. Winter, *J. Mol. Biol.,* 244: 361 (1994) discussing a phage display procedure used with a G protein-coupled receptor).

Other sources of potential ligands or other substances which bind to, or inhibitors and/or promoters of, mammalian CCR2 proteins include, but are not limited to, variants of CCR2 ligands, including naturally occurring, synthetic or recombinant variants of MCP-1, MCP-2, MCP-3 and/or MCP-4, substances such as other chemoattractants or chemokines, variants thereof, low molecular weight organic molecules, other inhibitors and/or promoters (e.g., anti-CCR2 antibodies, antagonists, agonists), other G protein-coupled receptor ligands, inhibitors and/or promoters (e.g., antagonists or agonists), and soluble portions of a mammalian CCR2 receptor, such as a suitable receptor peptide or analog which can inhibit receptor function (see e.g., Murphy, R. B., WO 94/05695).

Models of Inflammation

In vivo models of inflammation are available which can be used to assess the effects of antibodies and fragments of the invention in vivo as therapeutic agents. For example, leukocyte infiltration upon intradermal injection of a chemokine and an antibody or fragment thereof reactive with mammalian CCR2 into a suitable animal, such as rabbit, mouse, rat, guinea pig or rhesus macaque can be monitored (see e.g., Van Damme, J. et al., *J. Exp. Med.,* 176: 59–65 (1992); Zachariae, C. O. C. et al., *J. Exp. Med.* 171: 2177–2182 (1990); Jose, P. J. et al., *J. Exp. Med.* 179: 881–887 (1994)). In one embodiment, skin biopsies are assessed histologically for infiltration of leukocytes (e.g., eosinophils, granulocytes). In another embodiment, labeled cells (e.g., stably transfected cells expressing a mammalian CCR2, labeled with $^{111}$In for example) capable of chemotaxis and extravasation are administered to the animal. For example, an antibody or fragment to be assessed can be administered, either before, simultaneously with or after ligand or agonist is administered to the test animal. A decrease of the extent of infiltration in the presence of antibody as compared with the extent of infiltration in the absence of inhibitor is indicative of inhibition.

Diagnostic and Therapeutic Applications

The antibodies and fragments of the present invention are useful in a variety of applications, including research, diagnostic and therapeutic applications. In one embodiment, the antibodies are labeled with a suitable label (e.g., fluorescent label, chemiluminescent label, isotope label, antigen or epitope label or enzyme label). For instance, they can be used to isolate and/or purify receptor or portions thereof, and to study receptor structure (e.g., conformation) and function.

In addition, the various antibodies of the present invention can be used to detect CCR2 or to measure the expression of receptor, for example, on T cells (e.g., CD8+ cells, CD45RO+ cells), monocytes and/or on cells transfected with a receptor gene. Thus, they also have utility in applications such as cell sorting (e.g., flow cytometry, fluorescence activated cell sorting), for diagnostic or research purposes.

The anti-CCR2 antibodies of the present invention have value in diagnostic applications. An anti-CCR2 antibody or fragment thereof can be used to monitor expression of this receptor in HIV infected individuals, similar to the way anti-CD4 has been used as a diagnostic indicator of disease stage.

Typically, diagnostic assays entail detecting the formation of a complex resulting from the binding of an antibody or fragment thereof to CCR2. For diagnostic purposes, the antibodies or antigen-binding fragments can be labeled or unlabeled. The antibodies or fragments can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654 and 4,098,876). When unlabeled, the antibodies or fragments can be detected using suitable means, as in agglutination assays, for example. Unlabeled antibodies or fragments can also be used in combination with another (i.e., one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

In one embodiment, the antibodies or fragments of the present invention can be utilized in enzyme immunoassays, wherein the subject antibody or fragment, or second antibodies, are conjugated to an enzyme. When a biological sample comprising a mammalian CCR2 protein is combined with the subject antibodies, binding occurs between the antibodies and CCR2 protein. In one embodiment, a sample containing cells expressing a mammalian CCR2 protein, such as human blood, is combined with the subject antibodies, and binding occurs between the antibodies and cells bearing a human CCR2 protein comprising an epitope recognized by the antibody. These bound cells can be separated from unbound reagents and the presence of the antibody-enzyme conjugate specifically bound to the cells can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

Kits for use in detecting the presence of a mammalian CCR2 protein in a biological sample can also be prepared. Such kits will include an antibody or functional fragment thereof which binds to a mammalian CC-chemokine receptor 2 or portion of said receptor, as well as one or more ancillary reagents suitable for detecting the presence of a complex between the antibody or fragment and CCR2 or portion thereof. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of a mammalian CCR2 or a portion of the receptor by a cell, in which a composition comprising a cell or fraction thereof (e.g., membrane fraction) is contacted with an antibody or functional fragment thereof (e.g., 1D9 and/or 8G2) which binds to a mammalian CCR2 or portion of the receptor under conditions appropriate for binding of the antibody or fragment thereto, and binding is monitored. Detection of the antibody, indicative of the formation of a complex between antibody and CCR2 or a portion thereof, indicates the presence of the receptor. Binding of antibody to the cell can be determined as described above under the heading "Binding Assays", for example. The method can be used to detect expression of CCR2 on cells from an individual (e.g., in a sample, such as a body fluid, such as blood, saliva or other suitable sample). The level of expression of CCR2 on the surface of T cells or monocytes can also be determined, for instance, by flow cytometry, and the level of expression (e.g., staining intensity) can be correlated with disease susceptibility, progression or risk.

Chemokine receptors function in the migration of leukocytes throughout the body, particularly to inflammatory sites. Inflammatory cell emigration from the vasculature is regulated by a three-step process involving interactions of leukocyte and endothelial cell adhesion proteins and cell specific chemoattractants and activating factors (Springer, T. A., *Cell,* 76:301–314 (1994); Butcher, E. C., *Cell,* 67:1033–1036 (1991); Butcher, E. C. and Picker, L. J., *Science* (Wash. D.C.), 272:60–66 (1996)). These are: (a) a low affinity interaction between leukocyte selectins and endothelial cell carbohydrates; (b) a high-affinity interaction between leukocyte chemoattractant receptors and chemoattractant/activating factors; and (c) a tight-binding between leukocyte integrins and endothelial cell adhesion proteins of the immunoglobulin superfamily. Different leukocyte subsets express different repertoires of selectins, chemoattractant receptors and integrins. Additionally, inflammation alters the expression of endothelial adhesion proteins and the expression of chemoattractant and leukocyte activating factors. As a consequence, there is a great deal of diversity for regulating the selectivity of leukocyte recruitment to extravascular sites. The second step is crucial in that the activation of the leukocyte chemoattractant receptors is thought to cause the transition from the selectinmediated cell rolling to the integrin-mediated tight binding. This results in the leukocyte being ready to transmigrate to perivascular sites. The chemoattractant/chemoattractant receptor interaction is also crucial for transendothelial migration and localization within a tissue (Campbell, J. J., et al., *J. Cell Biol.*, 134:255–266 (1996); Carr, M. W., et al., *Immunity,* 4:179–187 (1996)). This migration is directed by a concentration gradient of chemoattractant leading towards the inflammatory focus.

CCR2 has an important role in leukocyte trafficking. It is likely that CCR2 is a key chemokine receptor for T cell or T cell subset or monocyte migration to certain inflammatory sites, and so anti-CCR2 mAbs can be used to inhibit (reduce or prevent) T cell or monocyte migration, particularly that associated with T cell dysfunction, such as autoimmune disease, or allergic reactions or with monocyte-mediated disorders such as atherosclerosis. Accordingly, the antibodies and fragments thereof of the present invention can also be used to modulate receptor function in research and therapeutic applications. For instance, the antibodies and functional fragments described herein can act as inhibitors to inhibit (reduce or prevent) (a) binding (e.g., of a ligand, an inhibitor or a promoter) to the receptor, (b) a receptor signaling function, and/or (c) a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand). Antibodies which bind receptor can also act as agonists of receptor function, triggering or stimulating a receptor function, such as a signaling and/or a stimulatory function of a receptor (e.g., leukocyte trafficking) upon binding to receptor.

Thus, the present invention provides a method of inhibiting leukocyte trafficking in a mammal (e.g., a human patient), comprising administering to the mammal an effective amount of an antibody or functional fragment of the present invention. Administration of an antibody or fragment of the present invention can result in amelioration or elimination of the disease state.

The antibody of the present invention, or a functional fragment thereof, can also be used to treat disorders in which activation of the CCR2 receptor by binding of chemokines is implicated. For example, the antibodies or functional fragments thereof (e.g., 1D9 and/or 8G2 or functional fragments thereof) can be used to treat allergy, atherogenesis, anaphylaxis, malignancy, chronic and acute inflammation, histamine and IgE-mediated allergic reactions, shock, and rheumatoid arthritis, atherosclerosis, multiple sclerosis, allograft rejection, fibrotic disease, asthma, and inflammatory glomerulopathies.

Diseases or conditions of humans or other species which can be treated with inhibitors of CCR2 receptor function (including antibodies or suitable fragments thereof), include, but are not limited to:

inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis);

autoimmune diseases, such as arthritis (e.g., rheumatoid arthritis, psoriatic arthritis), multiple sclerosis, systemic lupus erythematosus, myasthenia gravis, juvenile onset diabetes, nephritides such as glomerulonephritis, autoimmune thyroiditis, Behcet's disease;

graft rejection (e.g., in transplantation), including allograft rejection or graft-versus-host disease, and organ transplant-associated arteriosclerosis;

atherosclerosis;

cancers with leukocyte infiltration of the skin or organs;

stenosis or restenosis of the vasculature, particularly of the arteries, e.g., the coronary artery, such as stenosis or restenosis which results from vascular intervention (e.g., surgical, therapeutic or mechanical intervention), as well as neointimal hyperplasia. For example, restenosis, which typically produces a narrowing of the lumenal opening of the vessel, can result from vascular injury including, but not limited to, that produced by vascular graft procedures, angioplasty, including angioplasty performed by balloon, atherectomy, laser or other suitable method (e.g., percutaneous translumenal coronary angioplasty (PTCA)), stent placement (e.g., mechanical or biological endovascular stent placement), vascular bypass procedures or combinations thereof, as well as other procedures used to treat stenotic or occluded blood vessels;

other diseases or conditions (including CCR2-mediated diseases or conditions), in which undesirable inflammatory responses are to be inhibited can be treated, including, but not limited to, reperfusion injury, certain hematologic malignancies, cytokine-induced toxicity (e.g., septic shock, endotoxic shock), polymyositis, dermatomyositis, and granulomatous diseases including sarcoidosis.

Diseases or conditions of humans or other species which can be treated with promoters of CCR2 receptor function (including antibodies or fragments thereof), include, but are not limited to:

immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; and immunosuppression due congenital deficiency in receptor function or other causes.

Anti-CCR2 antibodies of the present invention can block the binding of one or more chemokines, thereby blocking the downstream cascade of one or more events leading to the above disorders.

Antibodies and functional fragments thereof which are antagonists of CCR2 can be used as therapeutics for AIDS, as well as certain inflammatory diseases. HIV-1 and HIV-2 are the etiologic agents of acquired immunodeficiency syndrome (AIDS) in humans. AIDS results in part from the depletion of CD4+ T lymphocytes in HIV infected individuals. HIV-1 infects primarily T lymphocytes, monocytes/macrophages, dendritic cells and, in the central nervous system, microglia. All of these cells express the CD4 glycoprotein, which serves as a receptor for HIV-1 and HIV-2. Efficient entry of HIV into target cells is dependent upon binding of the viral exterior envelope glycoprotein, gp120, to the amino-terminal CD4 domain. After virus binding, the HIV-1 envelope glycoproteins mediate the fusion of viral and host cell membranes to complete the entry process. Membrane fusion directed by HIV-1 envelope glycoproteins expressed on the infected cell surface leads to cell-cell fusion, resulting in syncytia.

Recently, host cell factors in addition to CD4 have been suggested to determine the efficiency of HIV-1 envelope glycoprotein-mediated membrane fusion. The 7 transmembrane receptor (7TMR) termed HUMSTSR, LESTR, or "fusin" has been shown to allow a range of CD4-expressing cells to support infection and cell fusion mediated by laboratory-adapted HIV-1 envelope glycoproteins (Feng, Y., et al., *Science* (Wash. D.C.), 272:872–877 (1996)). Antibodies to HUMSTSR blocked cell fusion and infection by laboratory-adapted HIV-1 isolates but not by macrophagetropic primary viruses in vitro (Feng, Y., et al., *Science* (Wash. D.C.), 272:872–877 (1996)).

The ability of chemokine receptors and related molecules to facilitate the infection of primary clinical HIV-1 isolates has been reported recently by several groups (see e.g., Bates, P., *Cell,* 86:1–3 (1996); Choe, H., et al., *Cell,* 85:1135–1148 (1996); Doranz et al., *Cell* 85:1149–1158 (1996)). These studies indicated that involvement of various members of the chemokine receptor family in the early stages of HIV-1 infection helps to explain viral tropism and β-chemokine inhibition of primary HIV-1 isolates.

The present invention also provides a method of inhibiting HIV infection of a cell (e.g., new infection and/or syncytium formation) which expresses a mammalian CCR2 or portion thereof, comprising contacting the cell with a composition comprising an effective amount of an antibody or functional fragment thereof which binds to a mammalian CCR2 or portion of said receptor. The composition can also comprise one or more additional agents effective against HIV, including, but not limited to, antiCCR3 antibodies, anti-CCR5 antibodies, and anti-fusin antibodies.

Various methods can be used to assess binding of HIV to a cell and/or infection of a cell by HIV in the presence of the antibodies of the present invention. For example, assays which assess binding of gp120 or a portion thereof to the receptor, HIV infection and syncytium formation can be used (see, for example, Choe, H., et al., *Cell,* 85:1135–1148 (1996)). The ability of the antibody of the present invention to inhibit these processes can be assessed using these or other suitable methods.

In addition, the present invention provides a method of treating HIV in a patient, comprising administering to the patient a composition comprising an effective amount of an antibody or functional fragment thereof which binds to a mammalian CCR2 or portion of said receptor. Again, the composition can also comprise one or more additional agents effective against HIV, including, but not limited to, anti-CCR3 antibodies, anti-CCR5 antibodies, and anti-fusin antibodies. Therapeutic use of antibody to treat HIV includes prophylactic use (e.g., for treatment of a patient who may be or who may have been exposed to HIV). For example, health care providers who may be exposed or who have been exposed to HIV (e.g., by needle-stick) can be treated according to the method. Another example is the treatment of a patient exposed to virus after unprotected sexual contact or failure of protection.

In AIDS, multiple drug treatment appears the most promising. An anti-chemokine receptor antagonist that inhibits HIV infection can be added to the drug treatment regimen, in particular by blocking virus infection of new cells. Thus, administration of an antibody or fragment of the present invention in combination with one or more other therapeutic agents such as nucleoside analogues (e.g., AZT, 3TC, ddI) and/or protease inhibitors is envisioned, and provides an important addition to an HIV treatment regimen. In one embodiment, a humanized anti-CCR2 mAb is used in combination with a (i.e., one or more) therapeutic agent to reduce viral load from patients, by preventing fusion and/or infection of new cells. Such an antibody can also be useful in preventing perinatal infection.

Another aspect of the invention relates to a method of preventing HIV infection in an individual, comprising administering to the individual an effective amount of an antibody or functional fragment thereof which binds to CCR2. According to the method, preventing HIV infection includes treatment in order to prevent (reduce or eliminate) infection of new cells in an infected individual or in order to prevent infection in an individual who may be, may have been, or has been, exposed to HIV. For example, individuals such as an HIV infected individual, a fetus of an HIV infected female, or a health care worker may be treated according to the method of the present invention.

Modes of Administration

One or more antibodies or fragments of the present invention can be administered to an individual by an appropriate route, either alone or in combination with (before, simultaneously with, or after) another drug or agent, or before, simultaneously with or after surgical, mechanical or therapeutic intervention. For example, the antibodies of the present invention can also be used in combination with other monoclonal or polyclonal antibodies (e.g., in combination with antibodies which bind other chemokine receptors, including, but not limited to, CCR3 and CCR5) or with existing blood plasma products, such as commercially available gamma globulin and immune globulin products used in prophylactic or therapeutic treatments. The antibodies or fragments of the present invention can be used as separately administered compositions given in conjunction with antibiotics and/or antimicrobial agents.

An effective amount of an antibody or fragment (i.e., one or more antibodies or fragments) is administered. An effective amount is an amount sufficient to achieve the desired therapeutic (including prophylactic) effect, under the conditions of administration, such as an amount sufficient for inhibition of a CCR2 function, and thereby, inhibition of an inflammatory response or HIV infection, or an amount sufficient for promotion of a CCR2 function, as indicated.

A variety of routes of administration are possible including, but not necessarily limited to, oral, dietary, topical, parenteral (e.g., intravenous, intraarterial, intramuscular, subcutaneous injection or infusion), inhalation (e.g., intrabronchial, intraocular, intranasal or oral inhalation, intranasal drops), depending on the disease or condition to be treated. Other suitable methods of administration can also include rechargeable or biodegradable devices and slow release polymeric devices. The pharmaceutical compositions of this invention can also be administered as part of a combinatorial therapy with other agents.

Formulation of an antibody or fragment to be administered will vary according to the route of administration and formulation (e.g., solution, emulsion, capsule) selected. An appropriate pharmaceutical composition comprising an antibody or functional fragment thereof to be administered can be prepared in a physiologically acceptable vehicle or carrier. A mixture of antibodies and/or fragments can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, *Remington's Pharmaceutical Science*, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies and fragments of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

The present invention will now be illustrated by the following Examples, which are not intended to be limiting in any way. The teachings of all references cited herein are incorporated herein by reference.

EXAMPLES

Materials

The following materials were obtained from the indicated sources:

PE-conjugated anti-CD16, PE-conjugated streptavidin, and biotinylated anti-human IgE were from Pharmingen (San Diego, Calif.). FITC-conjugated goat anti-mouse IgG was from Jackson Immunoresearch Laboratories (West Grove, Pa.). FACS Lysing Buffer was from Becton Dickenson (Mountain View, Calif.) and [$^{125}$I]-MCP-1 was from NEN (Boston, Mass.).

Cells, Cell Lines, and Tissue Culture

The murine pre-B lymphoma cell line L1/2 was maintained in RPMI-1640 supplemented with 10% Fetal Clone I (Gibco BRL, Gaithersburg, Md.) 50 Units/mL penicillin (Gibco BRL), 50 µg/mL streptomycin (Gibco BRL), 2 mM L-Glutamine (Gibco BRL), and 55 µM β-mercaptoethanol (Gibco BRL). Other cell lines included transfectants of L1/2 cells expressing either CCR1 (Campbell, J. et al. (1996) *J. Cell Bio.*, 134:255–266), CCR5 (Wu et al., *Nature* 384:179–183 (1996)) grown in the above culture medium supplemented with 800 µg/ml active G418. THP-1 cells (ATCC No. TIB202) were grown in accordance with ATCC instructions. PBMC were purified from heparinized blood as described in Ponath et al., *J. Clin. Invest.*, 97:604–612 (1996).

Preparation of CCR2 b Expression Construct and Stable Transfectants

The coding region for the human CCR2b (Charo et al. (1994) *Proc. Natl. Acad. Sci. USA*, 91:2752) was obtained by RT-PCR amplification as described (Qin, S. et al. (1996) *Eur. J. Immunol.*, 26:640–647). cDNA was made using oligo (dT)-priming, and amplification of the CCR2b coding region was achieved by nested PCR with the following sets of primers which correspond to the positions of the CCR2b sequence (GenBank Accession No. U03905; Charo et al., *Proc. Natl. Acad. Sci. USA* 91:2752–2756 (1994)) as indicated:

1) 5' primer: 5'-TGAGACAAGCCACAAGCTGAAC-3' (nucleotides 11 to 32; SEQ ID NO: 1);
3' Primer: 5'-TCTGTATTAGTACACACAGCCC-3' (nucleotides 1301 to 1280; SEQ ID NO: 2);
2) 5' Primer: 5'-ATGCTGTCCACATCTCGTTCTCGG-3' (nucleotides 81 to 104; SEQ ID NO: 3);
3' Primer: 5'-TTATAAACCAGCCGAGACTTCCTGCTC-3' (nucleotides 1164 to 1137; SEQ ID NO: 4).

The CCR2B cDNA coding region was modified to contain the CD5 signal peptide leader sequence (Aruffo et al., *Cell* 61:1303–1313 (1990)). The predicted amino acid sequence of this peptide is:

NH$_2$-Met-Pro-Met-Gly-Ser-Leu-Gln-Pro-Leu-Ala-Thr-Leu-Tyr-Leu-Leu-Gly-Met-Leu-Val-Ala-Ser-Val-Leu-Ala . . . (SEQ ID NO: 5)

Using PCR with the CCR2b cDNA as template and two overlapping 5' primers that contain a BamHI restriction site, encode the CD5 signal peptide sequence and the amino terminal sequence of CCR2b, and a 3' primer located internally in the CCR2b coding region.

5' CD5 Seq1 primer
5'-GGGGATCCAGAAACCATGCCCATGGGGTCTCTG CAACCGCTGGCCACCTTGTACCTGCTG-3' (SEQ ID NO: 6)
5' CD5 Seq2 primer
5'-GCCACCTTGTACCTGCTGGGGATGCTGGTCGCT TCCGTGCTAGCGATGCTGTCCACATCTCGTTC-3' (SEQ ID NO: 7)
3' CCR2AB2 primer-5'-GACGACCAGCATGTTGCC-3' (SEQ ID NO: 8; U03905 nucleotides 272 to 255)

The 278 base pair amplified fragment was digested with BamHI and Apal and the resulting 209 base pair fragment was inserted at the Apal site at position 206 of the CCR2b cDNA (GenBank Accession No. U03905) to replace the endogenous 5' base pair fragment of CCR2. The resulting sequence that encodes a CCR2b with the CD5 signal peptide leader sequence immediately preceding the receptor initiator methionine was inserted into the BamHI and Xhol sites of pcDNA3 (Invitrogen, San Diego, Calif.) to create the mammalian expression plasmid pCD5 MCPRB. The CD5-CCR2b fragment was subcloned into the BamH I-Not I site of pCDEF3 (Goldman et al., (1996) *Biotechniques* 21:1013–1015), and this construct was designated CCR2bDEF3. In this expression vector, the expression of the inserted gene is driven by the EF-1α promoter.

Fifty milliliters of L1/2 cells were seeded at 4×10$^5$ cells/mL the day before the electroporation. On the day of the electroporation, the cells, which had grown up to a density of 1×10$^6$/mL, were centrifuged out of their medium and resuspended in 800 µl room temperature electroporation buffer (Zajac et al., *DNA* 7:509–513). 120 mM L-Glutamic Acid (Sigma), 7 mM Mg Acetate (EM Science), 4.3 mM Glucose (Sigma), 17 mM K Pipes, pH 6.9 (Sigma), 1 mM EGTA (Sigma), 5 mM ATP, pH 7.0 (Sigma). Twenty-five micrograms Sca I linearized, phenol/chloroform/isoamyl alcohol extracted and isopropanol precipitated CCR2bDEF3 plasmid DNA was placed in an 0.4 cm gap electroporation curvette. The resuspended cells were added to the curvette, and a single pulse applied at 450 volts, 960 µFd. The cells were then transferred from the curvette to a T-75 flask containing 15 mL L1/2 growth medium (described above, and grown for three days, at which time the cells were centrifuged out of their medium and resuspended in L1/2 growth medium additionally supplemented with 1 mM sodium pyruvate (Gibco BRL) and 0.8 mg/mL active G418 (Gibco BRL).

Selection of Cells Expressing CCR2b by Chemotaxis

The transfected cells were allowed to grow for eleven days, at which point they were split 1:20 into fresh growth medium. On the sixteenth day, the cells were selected by chemotaxis. 600 µL 1 nM MCP-1 in RPMI 1640 supplemented with 0.5% BSA (RPMI/BSA) was placed in the lower chamber and 1×10$^6$ CCR2bDEF3 cells in 100 µl of RPMI/BSA were placed in the upper chamber of a 3.0 micron pore 24-well chemotaxis plate (Becton Dickinson). The cells were allowed to chemotax for four hours and twenty minutes in a 37° C., 5% $CO_2$, humidified incubator, at which time the upper chamber was removed. This incubation time was chosen at the time of the experiment because it was sufficiently long for cells responding to the MCP-1 to chemotax, but short enough to keep the background low.

Secondary Selection of CCR2b Expressing-Cells by FACS Sorting

The cells which had chemotaxed through the membrane and into the lower chamber were grown up, and further purified by sterile FACS sorting. Ten million CCR2bDEF3 cells were centrifuged out of their medium, resuspended in 2.5 mL PBS(+Ca, Mg) supplemented with 1% heat-inactivated Fetal Calf Serum ("HI FCS") (Gibco BRL) and 2.5 mL sterile filtered anti-CCR2b amino-terminal peptide antibody supernatant 5A11. The cells and the antibody were mixed and allowed to incubate on ice for thirty minutes. The cells were then washed twice with PBS (+) (Gibco BRL), and resuspended in 5 mL of a sterile filtered, 1:250 dilution of FITC-conjugated, affinity-purified $F(ab^1)_2$ goat anti-mouse IgG (Jackson ImmunoResearch Laboratories) in PBS (+) supplemented with 1% HI FCS. The cells were incubated for thirty minutes on ice in the dark, and then washed twice with PBS(+) (GIBCO BRL). The cells were sorted on the FACSCalibur® and the brightest 4% of cells were collected. ($FL1 \geq 3 \times 10^2$).

The sorted cells were allowed to grow up, and they were resorted using the same protocol as above. The brightest 1% of cells were collected. ($FL1 \geq 3 \times 10^3$).

Monoclonal Antibody Production

To produce mAbs to CCR2b, transfectants were continually monitored to ensure that levels of expression did not drift downward. FACS staining was performed periodically to ascertain receptor expression on the transfectants using the anti CCR2b antibody supernatant 5A11 with goat anti-mouse IgG FITC as the secondary antibody.

Twenty million CCR2bDEF3.L1/2 cells were washed in RPMI 1640 (Gibco BRL) and incubated in RPMI 1640 plus 0.2 mg/mL Mitomycin C for 30 minutes at 37° C. The cells were then washed twice with PBS (+) and $2 \times 10^7$ cells in 0.5 mL PBS (+) were injected intraperitoneally into a C57 BL/6 female mouse. This was repeated two more times at two week intervals. The fourth time, $2 \times 10^7$ cells were resuspended in 0.25 mL and injected intravenously. Three days after the intravenous injection, the mouse was sacrificed and the spleen removed and the cells fused with the SP2/0 cell line as described (*Current Protocols in Immunology*, John Wiley and Sons, New York, 1992).

This set of mice had previously been immunized many times with 2 different cell lines as well as a synthetic peptide, but no antibodies that stained CCR2 positive cells were generated from several fusions. The above four immunizations with the CCR2bDEF3.L1/2 cell line expressing high levels of CCR2b were critical to obtain the described antibody.

Selecting Single Cell Clone of CCR2 Transfectants by Limiting Dilution

After the mouse received the last injection, the twice sorted cells were allowed to grow up again, and then they were further purified by limiting dilution. The cells were plated at 1 and 0.5 cell per well in 96 well plates. Subcloned cells from the 0.5 cell per well dilution were grown up and tested for CCR2b expression by indirect immunofluorescent FACS analysis using the anti-CCR2b antibody supernatant 5A11 with goat anti-mouse IgG FITC as the secondary antibody. The procedure was the same as described above, except that the staining volume was 100 µl. Four positives were selected and frozen down.

Identification of Positive Monoclonal Antibodies

Immunofluorescent staining analysis using a FACScan® (Becton Dickinson & Co., Mountain View, Calif.) was used to identify the monoclonal antibodies which were reactive with the CCR2b receptor. Hybridoma culture supernatants were assayed in a 96-well format using goat anti-mouse IgG FITC as the secondary antibody. CCR2bDEF3.L1/2 cells were used to identify monoclonal antibodies reactive with CCR2b, and untransfected L1/2 cells were used to eliminate monoclonal antibodies reactive with other cell surface proteins.

FACS Staining—Cultured Cells

Figure 1O:
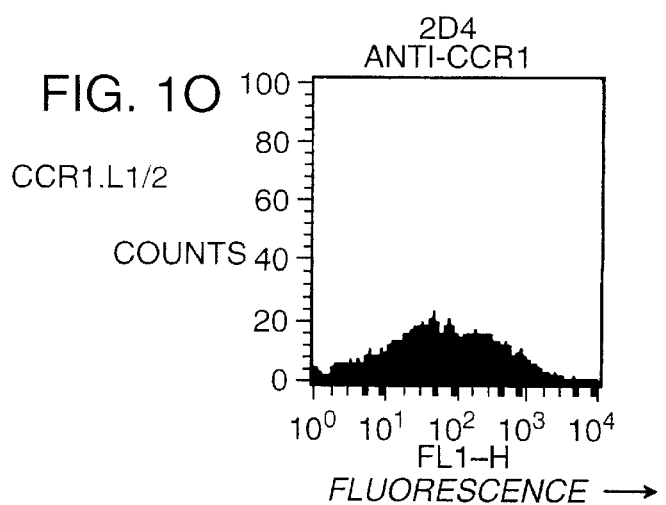
Figure 2C:
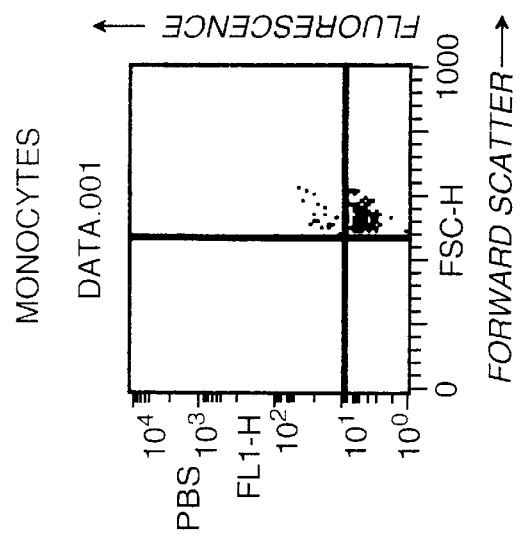
Figure 2B:
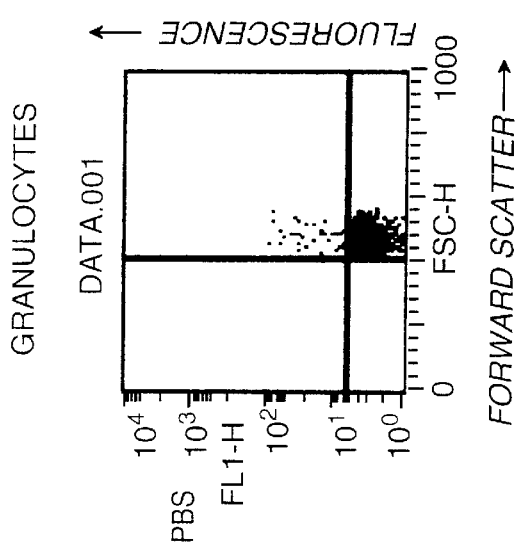
Figure 2A:
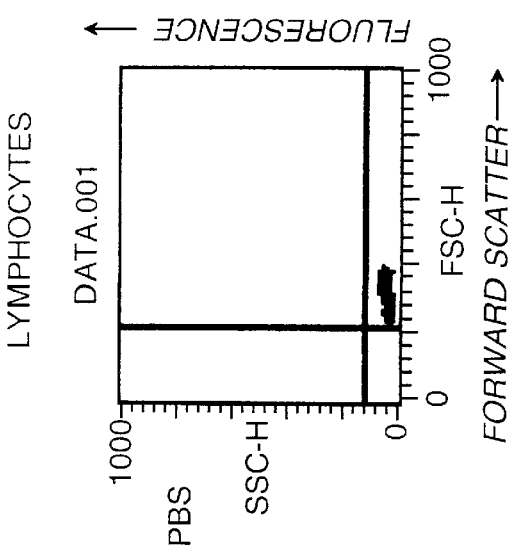
Figure 2F:
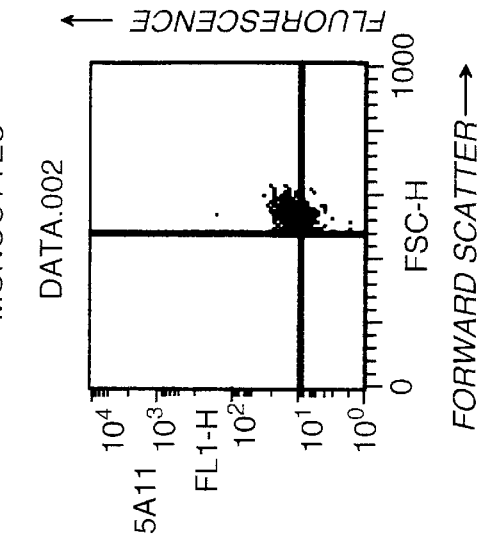
Figure 2E:
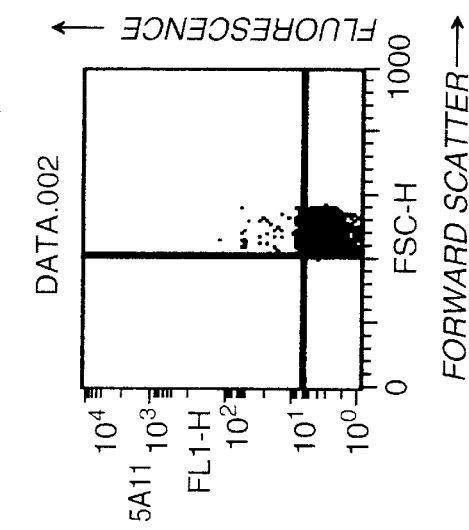
Figure 2D:
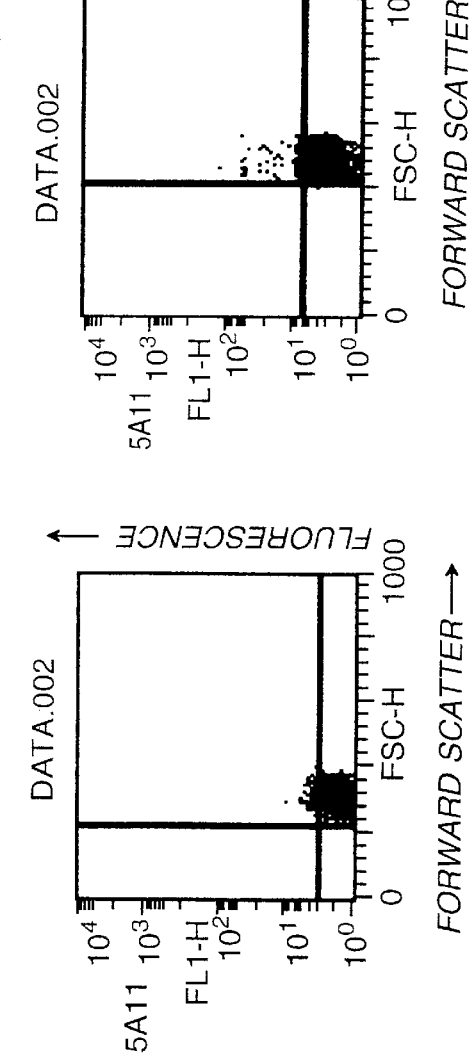
Figure 2I:
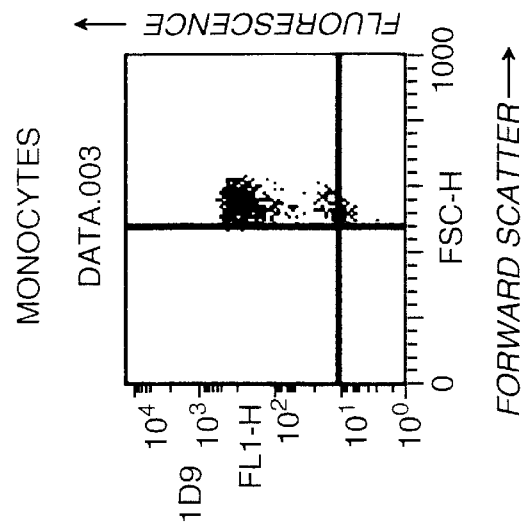
Figure 2H:
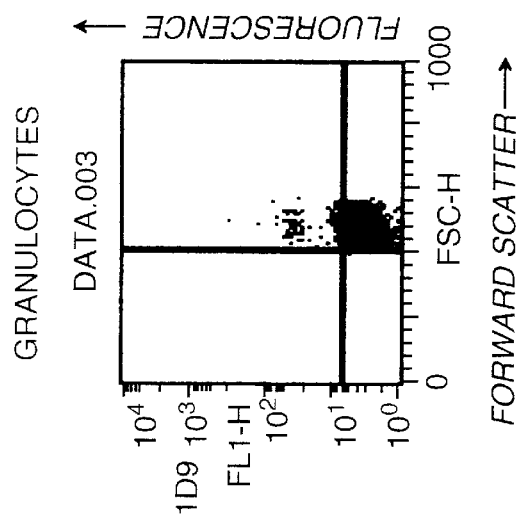
Figure 2G:
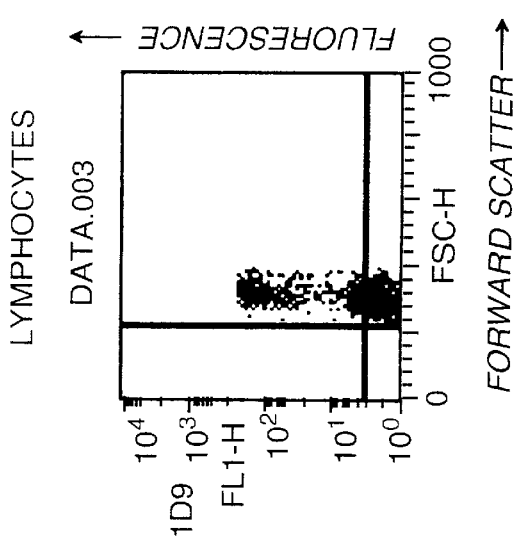
Figure 3A:
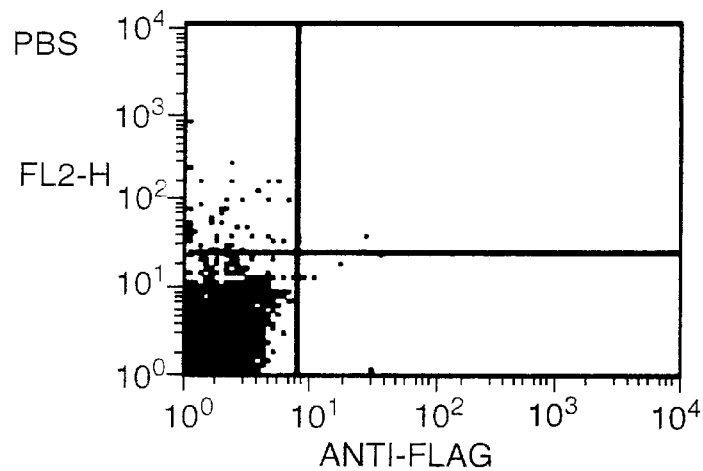
FIGS. 3A–3I FACS dot plots showing that mAb 1D9 stains an IgE positive population in peripheral blood (basophils) using two-color staining for IgE and CCR2. Whole blood cells were first stained with either a negative control antibody (anti-Flag), anti-CCR2 antibody 1D9, or an anti-CXCR1 antibody, as indicated, and detected by an anti-mouse-FITC conjugate. A second staining was done using either PBS or a biotinylated antibody specific for IgE or CD16, as indicated, and detected with a streptavidin-phycoerythrin. Staining was analyzed by flow cytometry.
Figure 3B:
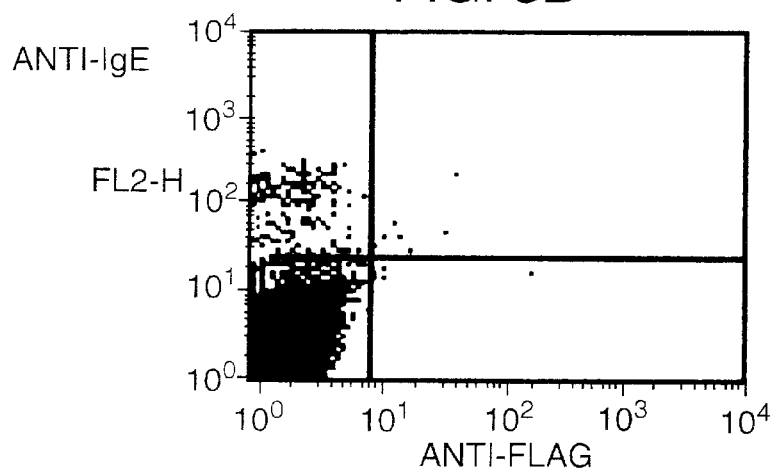
Figure 3C:
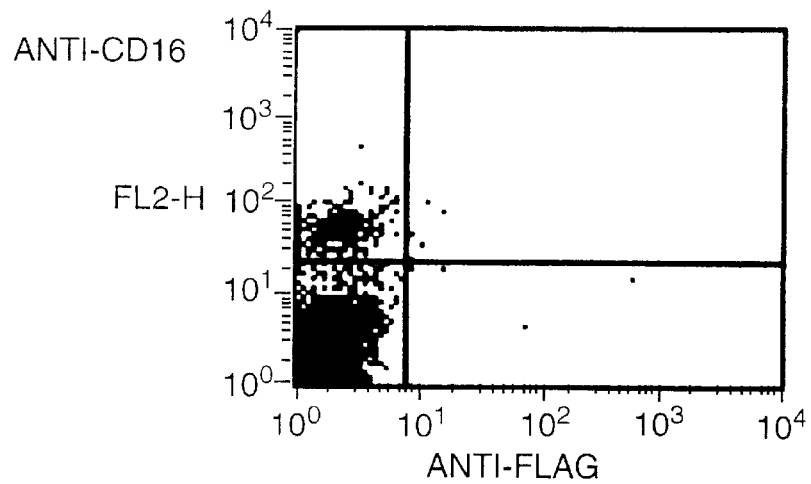
Figure 3D:
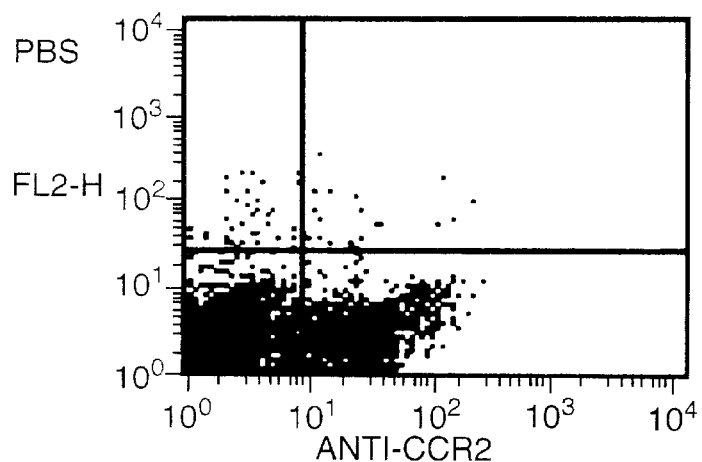
Figure 3E:
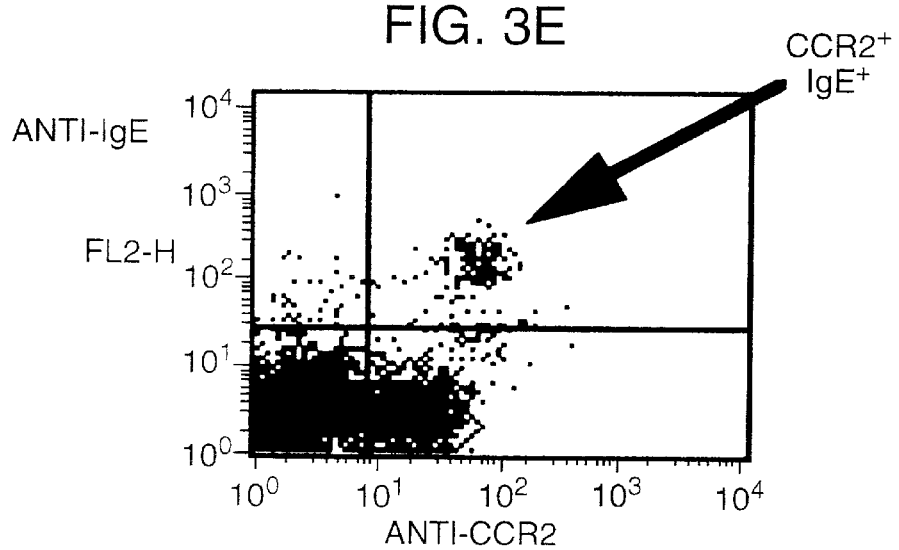
Figure 3F:
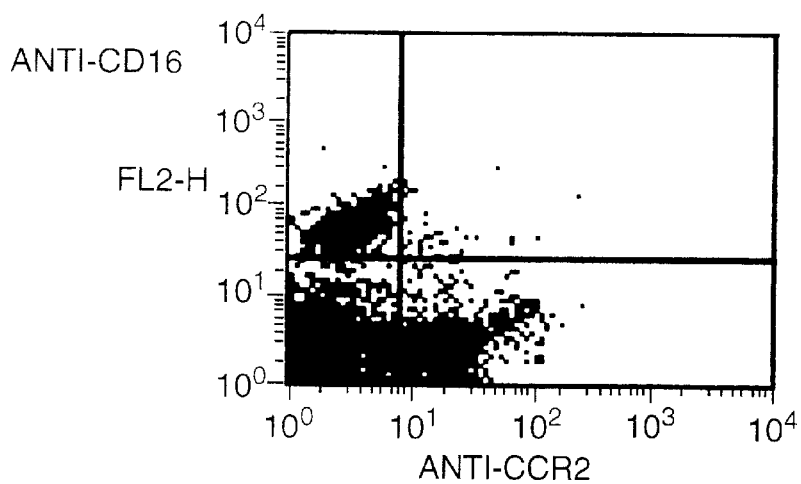
Figure 3G:
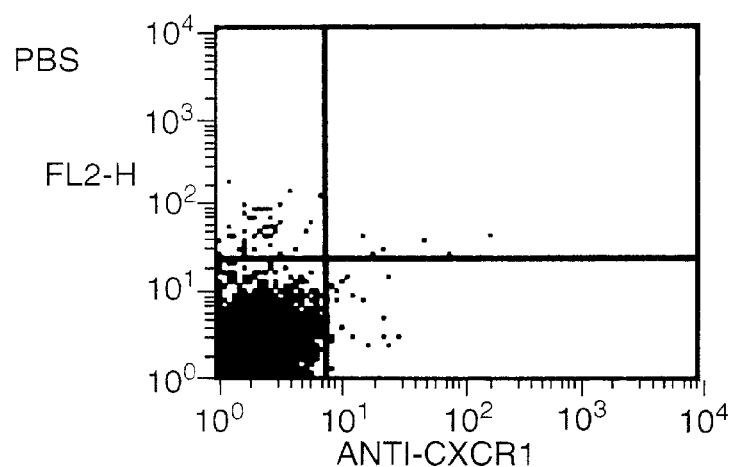
Figure 3H:
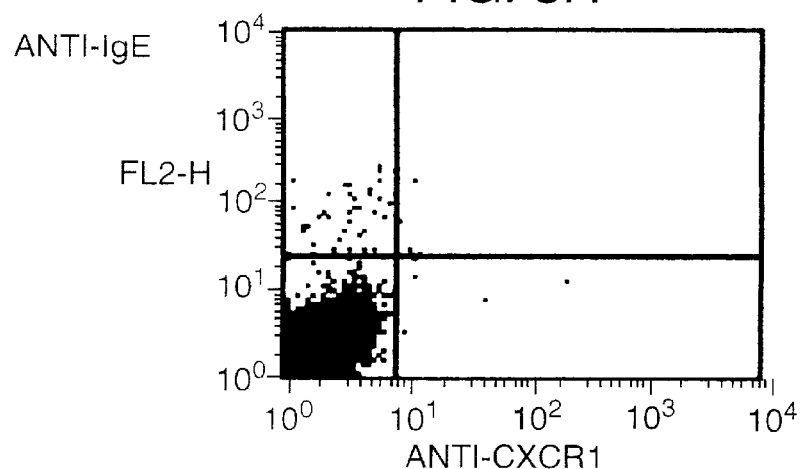
Figure 3I:
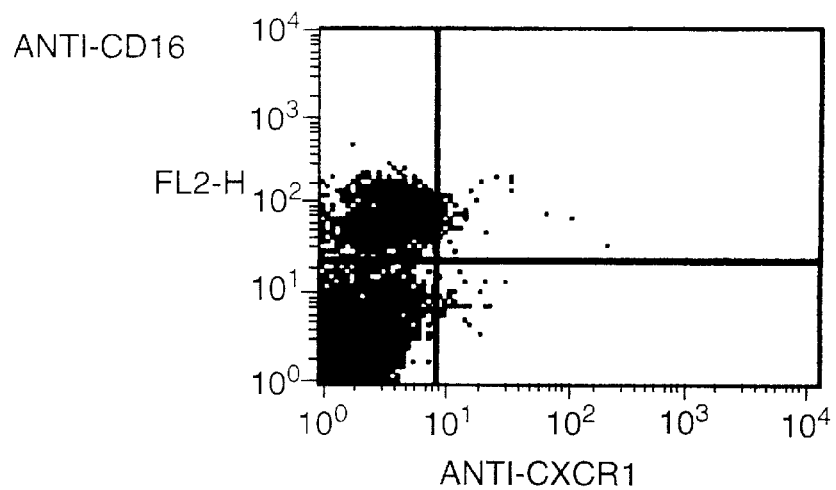

For the staining of cultured transfectant cell lines $0.5 \times 10^6$ cells in 50 µl were resuspended in PBS+1% FCS in a 96 well polystyrene V-bottom plate. 50 µl of primary antibody supernatants or HT medium (negative control) were added, and the samples were incubated at 4° C. for 30 min. 100 µl of PBS were added and the cells were pelleted by centrifugation and washed once with PBS. The pellet was resuspended in 100 µl PBS+1% FCS containing FITC-conjugated goat anti-mouse IgG antibody (a 1:250 dilution) and incubated for thirty minutes at 4° C. in the dark. The cells were washed twice with PBS, resuspended in PBS, and analyzed by flow cytometry with a FacScan cytometer using the CellQuest software (Becton-Dickenson) Cells were fixed with PBS/1% formaldehyde if they were not to be analyzed the same day. Monoclonal antibodies 1D9 and 8G2 stain CCR2 transfectants but not CCR1 or CCR5 transfectants (FIGS. 1A–1O).

FACS Staining—Whole Blood

100 µl whole blood was mixed with 100 µL of 1D9 antibody hybridoma supernatants or HT medium (negative control) and incubated at 4° C. for 30 min. After one wash with PBS, 100 µL FITC-conjugated goat anti-mouse IgG antibody (a 1:250 dilution) was added to each sample and incubated for 30 min. at 4° C. in the dark. Samples were then washed once with PBS if a second color staining is to be done, otherwise washed twice more in PBS. For two color staining 5 µl of mouse serum was added to the cell pellets after the single wash, mixed, and incubated for five minutes at 4° C. in the dark. Second primary antibodies (or PBS as a negative control) were added (10 µl anti-CD16, 100 µl 1:200 dilution of anti-IgE) and incubated for thirty minutes at 4° C. in the dark. Samples were then washed one time with PBS and resuspended in 100 µL streptavidin PE (1:200 PBS+1% BSA) and incubated for fifteen minutes at 4° C. in the dark. Eyrythrocytes were lysed by adding 2 ml of FACS Lysing Buffer to each sample and incubating at room temperature in the dark for fifteen minutes or until samples were clear. The cells were pelleted by centrifugation and all but 200 µl of the supernatant was aspirated. The samples were analyzed by flow cytometry on a FacScan cytometer using the CellQuest software (Becton-Dickenson). CCR2b is expressed on most monocytes, a subpopulation of lymphocytes and a subset of granulocytes (FIGS. 2A–2L). CCR2b is expressed on an IgE-positive population in peripheral blood (basophils) (FIGS. 3A–3I).

MCP-1 Binding Assays

Figure 4:
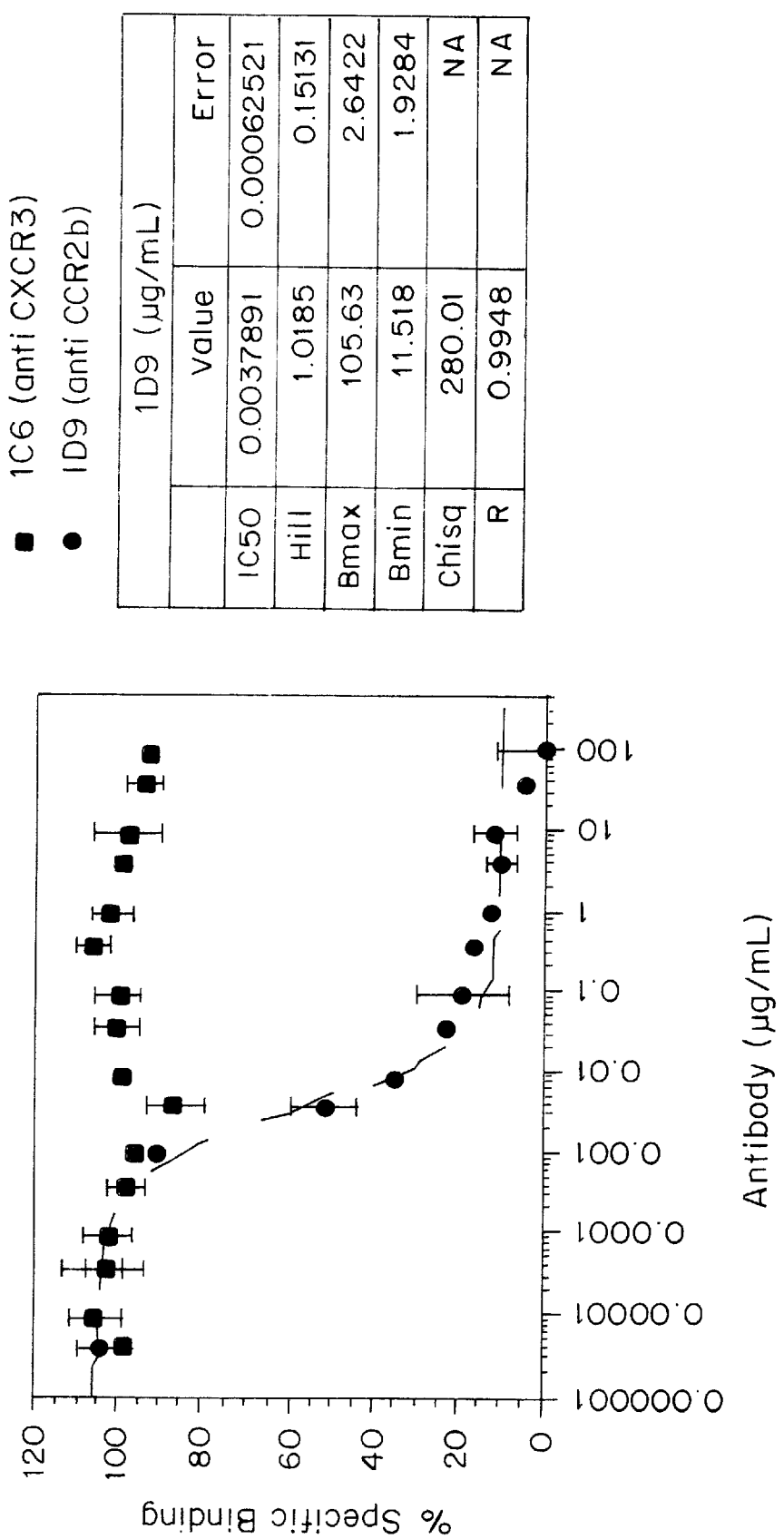
FIG. 4 illustrates that mAb 1D9 inhibits [$^{125}$I]MCP-1 binding to THP-1 cell membranes. 3.0 μg of THP-1 membrane protein was incubated with 0.1 nM [$^{125}$I]MCP-1 in the presence of various concentrations of 1D9 or the isotype-matched anti-CXCR3 antibody 1C6. The amount of bound tracer was determined by separation of free from bound by filtration and scintillation counting. The data was analyzed to determine the IC$_{50}$ value by non-linear regression using a 4-parameter logistic equation with KaleidaGraph software.
Figure 5:
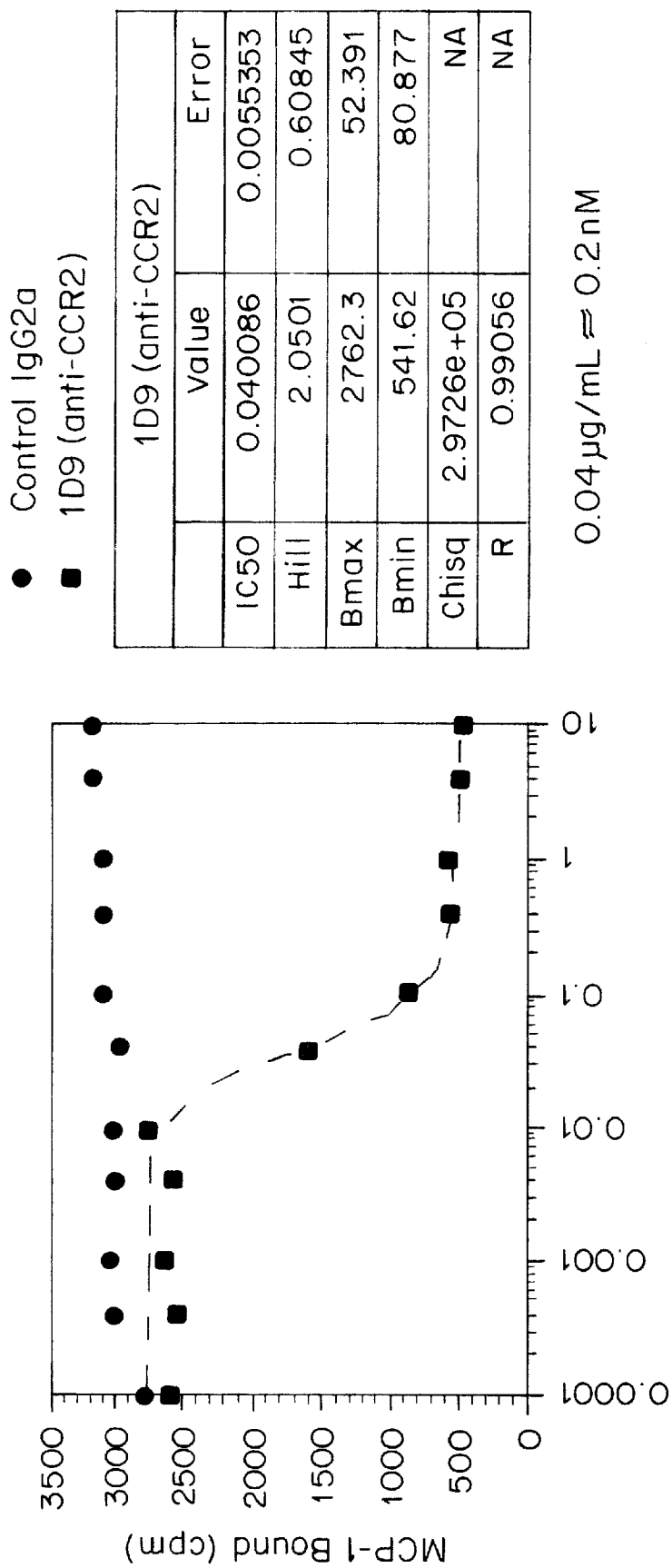
FIG. 5 illustrates that mAb 1D9 inhibits [$^{125}$I]MCP-1 binding to fresh human PBMC. Freshly isolated peripheral blood mononuclear cells (500,000) were incubated with 0.1 nM [$^{125}$I]MCP-1 in the presence of various concentrations of 1D9 or the isotype-matched anti-CXCR3 antibody 1C6. The amount of bound tracer was determined by separation of free from bound by filtration and scintillation counting. The data was analyzed to determine the IC$_{50}$ value as for FIG. 4.

MCP-1 binding was performed in a final volume of 0.1 ml of 50 mM Hepes pH 7.4, 1 mM $CaCl_2$, 5 mM $MgCl_2$, 0.02% sodium azide, 0.5% BSA (HBB), containing either 2.5 µg THP-1 membrane protein or 500,000 PBMC and 0.1 nM of [$^{125}$I]-MCP-1. Competition binding experiments were performed by including variable concentrations of unlabeled MCP-1, 1D9 antibody, or a negative control IgG2a. Nonspecific binding was determined following the addition of a 2500-fold excess of unlabeled MCP-1. Samples were incubated for 60 minutes at room temperature, and bound and free tracer were separated by filtration through 96-well GF/B filterplates presoaked in 0.3% polyethyleneimine. The filters were washed in HBB further supplemented with 0.5 M NaCl, dried, and the amount of bound radioactivity determined by liquid scintillation counting. mAb 1D9 inhibits [$^{125}$I]MCP-1 binding to THP-1 cell membranes with an $IC_{50}$ of about 0.004 μg/ml (approximately 0.02 nM; FIG. 4) and to fresh PBMC with an $IC_{50}$ of 0.04 μg/ml (approximately 0.2 nM; FIG. 5).

Chemotaxis of PBMC

Figure 6A:
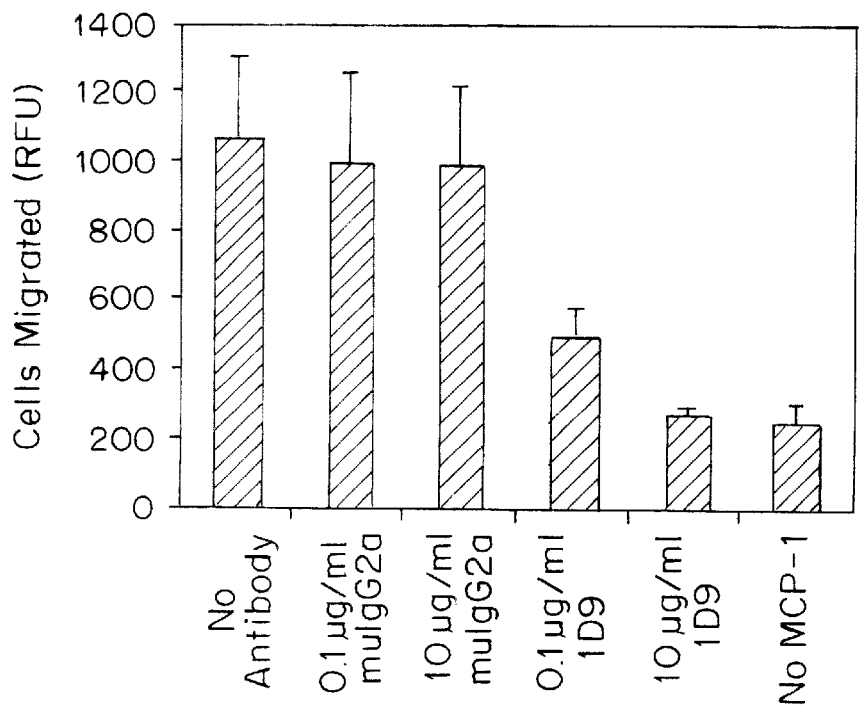
FIGS. 6A and 6B are graphs demonstrating that mAb 1D9 inhibits MCP-1-induced chemotaxis, but not RANTES-induced chemotaxis, of fresh PBMC.
Figure 6B:
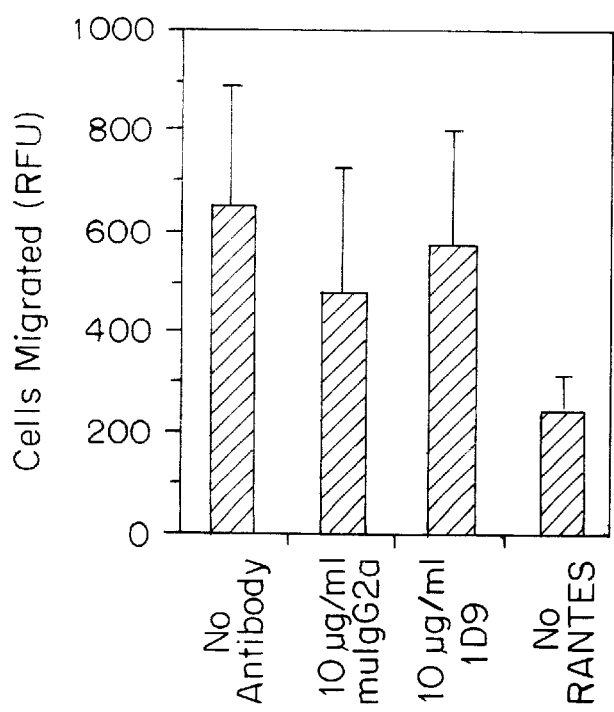

Chemotaxis was assayed using a 3 μm pore size 96-well chemotaxis plate (Neuroprobe, Cabin John, Md.). PBMC isolated by standard methods using Ficoll-Hypaque density gradient centrifugation were washed with PBS/0.5%BSA and then resuspended in chemotaxis assay media (HBSS/10 mM HEPES/0.5% Fatty acid free BSA) to a final concentration of 10×10$^6$ cells/ml. Cells were princubated in chemotaxis assay media at room temperature for 20 min. with various concentrations of the anti-CCR2 antibody, 1D9, or nonspecific murine IgG2a. The same dilutions of antibody were mixed with chemokine and 30 μl of the mixture was added to each of the bottom wells of the chemotaxis plate. The bottom wells are covered with the membrane, and 25 μl of the cell and antibody mixture are added to the top of the filter. The plates are incubated at 37° C. in 5% $CO_2$ incubator for approximately 80 min. At the completion of the migration, the membrane is removed and the plate with the bottom wells is incubated −80 C. for 30 minutes to freeze the contents. The plates are thawed at 37° C. for 10 minutes. 6 μl of a 1:400 dilution of CyQuant reagent (Molecular Probes, Eugene, Oreg.) in a lysis buffer provided by the supplier is added to each well, and the cell migration is quantified as indicated by fluorescence intensity determined using a CytoFlour fluorescence plate reader at 485ex/535em. mAb 1D9 inhibits MCP-1-induced chemotaxis, but not RANTES-induced chemotaxis, of fresh PBMC (FIGS. 6A and 6B). Inhibition of MCP-1-induced chemotaxis of fresh PBMC has been demonstrated with 10 μg/ml (≈40 nM).

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A method of inhibiting restenosis in a patient, comprising administering to the patient an effective amount of an antibody or antigen-binding fragment thereof which binds to mammalian CC-chemokine receptor 2, wherein said antibody or antigen-binding fragment thereof inhibits binding of a ligand to the receptor.

2. A method according to claim 1, wherein the antibody or antigen-binding fragment thereof is selected from the group consisting of:
   a) monoclonal antibody 1D9;
   b) an antibody having the epitopic specificity of monoclonal antibody 1D9;
   c) an antibody which can compete with monoclonal antibody 1D9 for binding to mammalian CC-chemokine receptor 2;
   d) monoclonal antibody 8G2;
   e) an antibody having the epitopic specificity of monoclonal antibody 8G2;
   f) an antibody which can compete with monoclonal antibody 8G2 for binding to mammalian CC-chemokine receptor 2;
   g) antigen-binding fragments of any one of (a) through (g) which bind to mammalian CC-chemokine receptor 2; and
   h) combinations of the foregoing.

3. A method of inhibiting restenosis of a vessel in a mammal, comprising administering to said mammal an effective amount of an antibody or antigen-binding fragment thereof which binds to a mammalian CC-chemokine receptor 2, wherein said antibody or antigen-binding fragment thereof inhibits binding of a ligand to the receptor.

4. A method according to claim 3 wherein the antibody or antigen-binding fragment thereof is selected from the group consisting of:
   a) monoclonal antibody 1D9;
   b) an antibody having the epitopic specificity of monoclonal antibody 1D9;

c) an antibody which can compete with monoclonal antibody 1D9 for binding to mammalian CC-chemokine receptor 2;
d) monoclonal antibody 8G2;
e) an antibody having the epitopic specificity of monoclonal antibody 8G2;
f) an antibody which can compete with monoclonal antibody 8G2 for binding to mammalian CC-chemokine receptor 2;
g) antigen-binding fragments of any one of (a) through (g) which bind to mammalian CC-chemokine receptor 2; and
h) combinations of the foregoing.

5. A method according to claim 3, wherein said restenosis is associated with vascular intervention in said mammal.

6. A method according to claim 5, wherein said vascular intervention comprises angioplasty.

7. A method according to claim 5, wherein said vascular intervention comprises stent placement.

8. A method according to claim 5, wherein said vascular intervention comprises angioplasty and stent placement.

9. A method of inhibiting narrowing of the lumen of a vessel in a mammal, comprising administering to said mammal an effective amount of an antibody or antigen-binding fragment thereof which binds to a mammalian CC-chemokine receptor 2, wherein said antibody or antigen-binding fragment thereof inhibits binding of a ligand to the receptor.

10. A method according to claim 9 wherein the antibody or antigen-binding fragment thereof is selected from the group consisting of:
a) monoclonal antibody 1D9;
b) an antibody having the epitopic specificity of monoclonal antibody 1D9;
c) an antibody which can compete with monoclonal antibody 1 D9 for binding to mammalian CC-chemokine receptor 2;
d) monoclonal antibody 8G2;
e) an antibody having the epitopic specificity of monoclonal antibody 8G2;
f) an antibody which can compete with monoclonal antibody 8G2 for binding to mammalian CC-chemokine receptor 2;
g) antigen-binding fragments of any one of (a) through (g) which bind to mammalian CC-chemokine receptor 2; and
h) combinations of the foregoing.

11. A method of inhibiting neointimal hyperplasia of a vessel in a mammal, comprising administering to said mammal an effective amount of an antibody or antigen-binding fragment thereof which binds to a mammalian CC-chemokine receptor 2, wherein said antibody or antigen-binding fragment thereof inhibits binding of a ligand to the receptor.

12. A method according to claim 11 wherein the antibody or antigen-binding fragment thereof is selected from the group consisting of:
a) monoclonal antibody 1D9;
b) an antibody having the epitopic specificity of monoclonal antibody 1D9;
c) an antibody which can compete with monoclonal antibody 1D9 for binding to mammalian CC-chemokine receptor 2;
d) monoclonal antibody 8G2;
e) an antibody having the epitopic specificity of monoclonal antibody 8G2;
f) an antibody which can compete with monoclonal antibody 8G2 for binding to mammalian CC-chemokine receptor 2;
g) antigen-binding fragments of any one of (a) through (g) which bind to mammalian CC-chemokine receptor 2; and
h) combinations of the foregoing.

13. A method according to claim 11, wherein said neointimal hyperplasia is associated with vascular intervention in said mammal.

14. A method according to claim 13, wherein said vascular intervention comprises angioplasty.

15. A method according to claim 13, wherein said vascular intervention comprises stent placement.

16. A method according to claim 13, wherein said vascular intervention comprises angioplasty and stent placement.

17. A method according to claim 1, wherein the ligand is a chemokine.

18. A method according to claim 17, wherein the chemokine is selected from the group consisting of MCP-1, MCP-2, MCP-3, MCP-4 and combinations thereof.

19. A method according to claim 1, wherein said antibody or antigen-binding fragment thereof binds the amino-terminal domain of the receptor.

20. A method according to claim 19, wherein said antibody or antigen-binding fragment binds a portion of the amino-terminal domain which is from about amino acid 1 to about amino acid 30 of the receptor.

21. A method according to claim 1, wherein said mammalian CC-chemokine receptor 2 is a human CC-chemokine receptor 2.

22. A method according to claim 1, wherein said antibody or antigen-binding fragment thereof is a monoclonal antibody or antigen-binding fragment thereof.

23. A method according to claim 1, wherein said antibody or antigen-binding fragment thereof is a human antibody or antigen-binding fragment thereof.

24. A method according to claim 1, wherein said antibody or antigen-binding fragment is a chimeric antibody or antigen-binding fragment thereof.

25. A method according to claim 1, wherein said antibody or antigen-binding fragment is a recombinant antibody or antigen-binding fragment thereof.

26. A method according to claim 1, wherein said antibody or antigen-binding fragment is a humanized antibody or antigen-binding fragment thereof.

27. A method according to claim 26, wherein said humanized antibody comprises one or more antigen-binding regions of monoclonal antibody 1D9.

28. A method according to claim 26, wherein said humanized antibody comprises one or more complementarity-determining regions of monoclonal antibody 1D9.

29. A method according to claim 28, wherein said humanized antibody comprises six complementarity-determining regions of monoclonal antibody 1D9.

30. A method according to claim 1, wherein said antigen-binding fragment is selected from the group consisting of an Fv fragment, an Fab fragment, an Fab' fragment and an F(ab')$_2$ fragment.

31. A method according to claim 3, wherein the ligand is a chemokine.

32. A method according to claim 31, wherein the chemokine is selected from the group consisting of MCP-1, MCP-2, MCP-3, MCP-4 and combinations thereof.

33. A method according to claim 3, wherein said antibody or antigen-binding fragment thereof binds the amino-terminal domain of the receptor.

34. A method according to claim 33, wherein said antibody or antigen-binding fragment binds a portion of the amino-terminal domain which is from about amino acid 1 to about amino acid 30 of the receptor.

35. A method according to claim 3, wherein said mammalian CC-chemokine receptor 2 is a human CC-chemokine receptor 2.

36. A method according to claim 3, wherein said antibody or antigen-binding fragment thereof is a monoclonal antibody or antigen-binding fragment thereof.

37. A method according to claim 3, wherein said antibody or antigen-binding fragment thereof is a human antibody or antigen-binding fragment thereof.

38. A method according to claim 3, wherein said antibody or antigen-binding fragment is a chimeric antibody or antigen-binding fragment thereof.

39. A method according to claim 3, wherein said antibody or antigen-binding fragment is a recombinant antibody or antigen-binding fragment thereof.

40. A method according to claim 3, wherein said antibody or antigen-binding fragment is a humanized antibody or antigen-binding fragment thereof.

41. A method according to claim 40, wherein said humanized antibody comprises one or more antigen-binding regions of monoclonal antibody 1D9.

42. A method according to claim 40, wherein said humanized antibody comprises one or more complementarity-determining regions of monoclonal antibody 1D9.

43. A method according to claim 42, wherein said humanized antibody comprises six complementarity-determining regions of monoclonal antibody 1D9.

44. A method according to claim 3, wherein said antigen-binding fragment is selected from the group consisting of an Fv fragment, an Fab fragment, an Fab' fragment and an F(ab')$_2$ fragment.

45. A method according to claim 9, wherein the ligand is a chemokine.

46. A method according to claim 45, wherein the chemokine is selected from the group consisting of MCP-1, MCP-2, MCP-3, MCP-4 and combinations thereof.

47. A method according to claim 9, wherein said antibody or antigen-binding fragment thereof binds the amino-terminal domain of the receptor.

48. A method according to claim 47, wherein said antibody or antigen-binding fragment binds a portion of the amino-terminal domain which is from about amino acid 1 to about amino acid 30 of the receptor.

49. A method according to claim 9, wherein said mammalian CC-chemokine receptor 2 is a human CC-chemokine receptor 2.

50. A method according to claim 9, wherein said antibody or antigen-binding fragment thereof is a monoclonal antibody or antigen-binding fragment thereof.

51. A method according to claim 9, wherein said antibody or antigen-binding fragment thereof is a human antibody or antigen-binding fragment thereof.

52. A method according to claim 9, wherein said antibody or antigen-binding fragment is a chimeric antibody or antigen-binding fragment thereof.

53. A method according to claim 9, wherein said antibody or antigen-binding fragment is a recombinant antibody or antigen-binding fragment thereof.

54. A method according to claim 9, wherein said antibody or antigen-binding fragment is a humanized antibody or antigen-binding fragment thereof.

55. A method according to claim 54, wherein said humanized antibody comprises one or more antigen-binding regions of monoclonal antibody 1D9.

56. A method according to claim 54, wherein said humanized antibody comprises one or more complementarity-determining regions of monoclonal antibody 1D9.

57. A method according to claim 56, wherein said humanized antibody comprises six complementarity-determining regions of monoclonal antibody 1D9.

58. A method according to claim 9, wherein said antigen-binding fragment is selected from the group consisting of an Fv fragment, an Fab fragment, an Fab' fragment and an F(ab')$_2$ fragment.

59. A method according to claim 11, wherein the ligand is a chemokine.

60. A method according to claim 59, wherein the chemokine is selected from the group consisting of MCP-1, MCP-2, MCP-3, MCP-4 and combinations thereof.

61. A method according to claim 11, wherein said antibody or antigen-binding fragment thereof binds the amino-terminal domain of the receptor.

62. A method according to claim 61, wherein said antibody or antigen-binding fragment binds a portion of the amino-terminal domain which is from about amino acid 1 to about amino acid 30 of the receptor.

63. A method according to claim 11, wherein said mammalian CC-chemokine receptor 2 is a human CC-chemokine receptor 2.

64. A method according to claim 11, wherein said antibody or antigen-binding fragment thereof is a monoclonal antibody or antigen-binding fragment thereof.

65. A method according to claim 11, wherein said antibody or antigen-binding fragment thereof is a human antibody or antigen-binding fragment thereof.

66. A method according to claim 11, wherein said antibody or antigen-binding fragment is a chimeric antibody or antigen-binding fragment thereof.

67. A method according to claim 11, wherein said antibody or antigen-binding fragment is a recombinant antibody or antigen-binding fragment thereof.

68. A method according to claim 11, wherein said antibody or antigen-binding fragment is a humanized antibody or antigen-binding fragment thereof.

69. A method according to claim 68, wherein said humanized antibody comprises one or more antigen-binding regions of monoclonal antibody 1D9.

70. A method according to claim 68, wherein said humanized antibody comprises one or more complementarity-determining regions of monoclonal antibody 1D9.

71. A method according to claim 70, wherein said humanized antibody comprises six complementarity-determining regions of monoclonal antibody 1D9.

72. A method according to claim 11, wherein said antigen-binding fragment is selected from the group consisting of an Fv fragment, an Fab fragment, an Fab' fragment and an F(ab')$_2$ fragment.

* * * * *